United States Patent
Llinas et al.

(10) Patent No.: US 6,687,525 B2
(45) Date of Patent: Feb. 3, 2004

(54) METHOD AND SYSTEM FOR DIAGNOSING AND TREATING THALAMOCORTICAL DYSRHYTHMIA

(75) Inventors: Rodolfo R. Llinas, New York, NY (US); Urs Ribary, New York, NY (US); Daniel Jeanmonod, Zumikon (CH)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/876,895

(22) Filed: Jun. 7, 2001

(65) Prior Publication Data

US 2002/0055675 A1 May 9, 2002

Related U.S. Application Data

(60) Provisional application No. 60/210,040, filed on Jun. 7, 2000.

(51) Int. Cl.[7] .................................................. A61B 5/05
(52) U.S. Cl. ........................ 600/407; 600/409; 600/544
(58) Field of Search ................................. 600/407, 409, 600/544, 410; 128/920, 923

(56) References Cited

U.S. PATENT DOCUMENTS

| | | | |
|---|---|---|---|
| 5,119,816 A | | 6/1992 | Gevins ........................ 128/644 |
| 5,267,570 A | * | 12/1993 | Preston |
| 5,309,923 A | * | 5/1994 | Leuchter et al. |
| 5,687,724 A | | 11/1997 | Jewett et al. ............ 128/653.1 |
| 5,797,853 A | * | 8/1998 | Musha et al. ................ 600/544 |
| 5,885,223 A | * | 3/1999 | Herrmann ................... 600/544 |
| 6,097,980 A | * | 8/2000 | Monastra et al. ........... 600/544 |
| 6,144,872 A | | 11/2000 | Graetzl ........................ 600/409 |
| 6,351,674 B2 | * | 2/2002 | Silverstone .................. 607/46 |

OTHER PUBLICATIONS

*Thalamocortical Dysrhythmia: A Neurological and Neuropsychiatric Syndrome Characterized By Magnetoencephalography* Rodolfo R. Llinas et al. (Dec. 21, 1999; vol. 96, No. 26) pp. 15222–15227.

* cited by examiner

Primary Examiner—Shawna J Shaw
(74) Attorney, Agent, or Firm—Darby & Darby

(57) ABSTRACT

Method and system for diagnosing and treating thalamocortical dysrhythmia. Thalamocortical dysrhythmia occurs when unbalanced neural activity occurs due to the rise of low frequency (approximately 4–8 Hz) and high frequency (approximately 20–50 Hz) neuronal oscillation activity simultaneously within awake individuals. The underlying mechanism that causes thalamocortical dysrhythmia is abnormal input into thalamic cells, which causes a low-frequency shift, increased amplitude, and increased frequency correlation of neuronal oscillation at the cortical and thalamic levels. The present invention measures the neuronal activity at the cortical level, filters these measurements, and performs a Fourier transform to transfer neuronal oscillation data into the frequency domain. The present invention then selects at least one reference baseline based on the characteristics of control subjects that do not have thalamocortical dysrhythmia and/or patients that have thalamocortical dysrhythmia. The present invention determines the amplitude, frequency, and correlation deviations of the measured neuronal oscillations relative to the selected baselines and then determines whether an individual has thalamocortical dysrhythmia based on the deviations from the selected baselines. The present invention is thereby able to diagnose individuals as having or not having thalamocortical dysrhythmia, as well as to prescribe treatment for thalamocortical dysrhythmia based on the diagnosis and underlying amplitude, frequency and correlation deviation measurements.

37 Claims, 15 Drawing Sheets

FIG. 1A
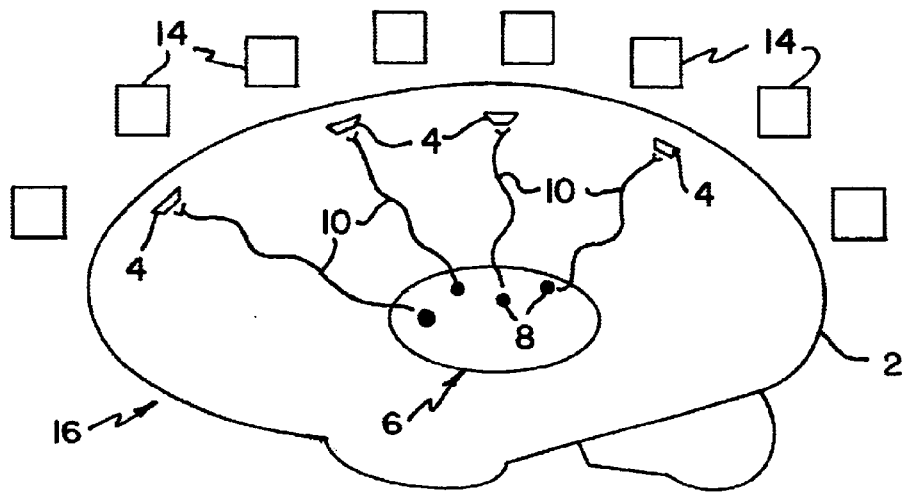
FIG. 1B
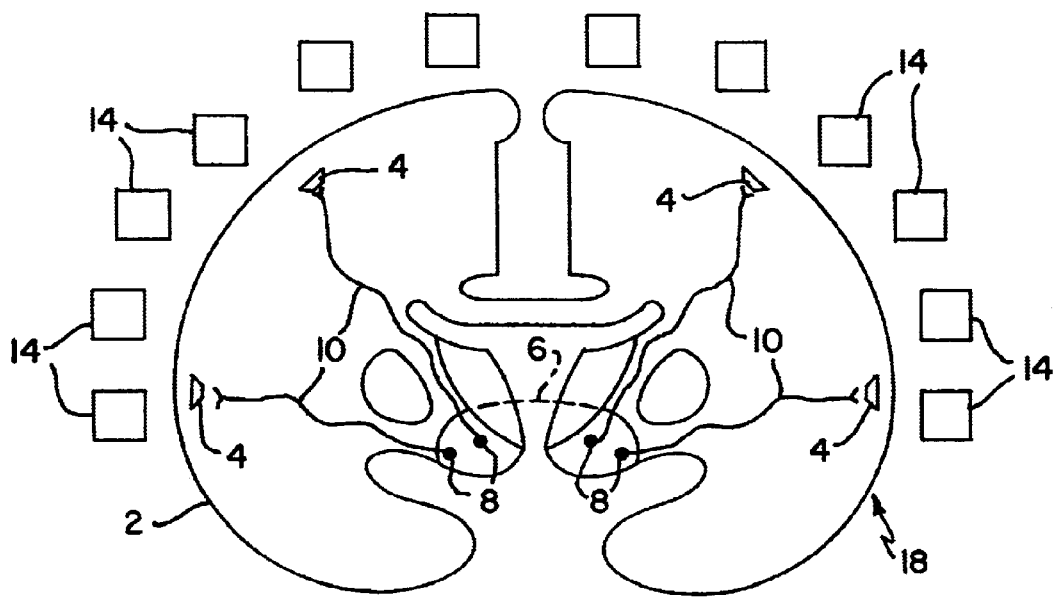
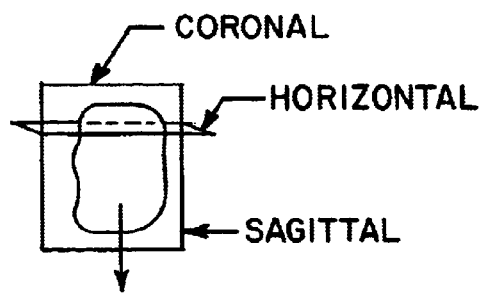
FIG. 1C

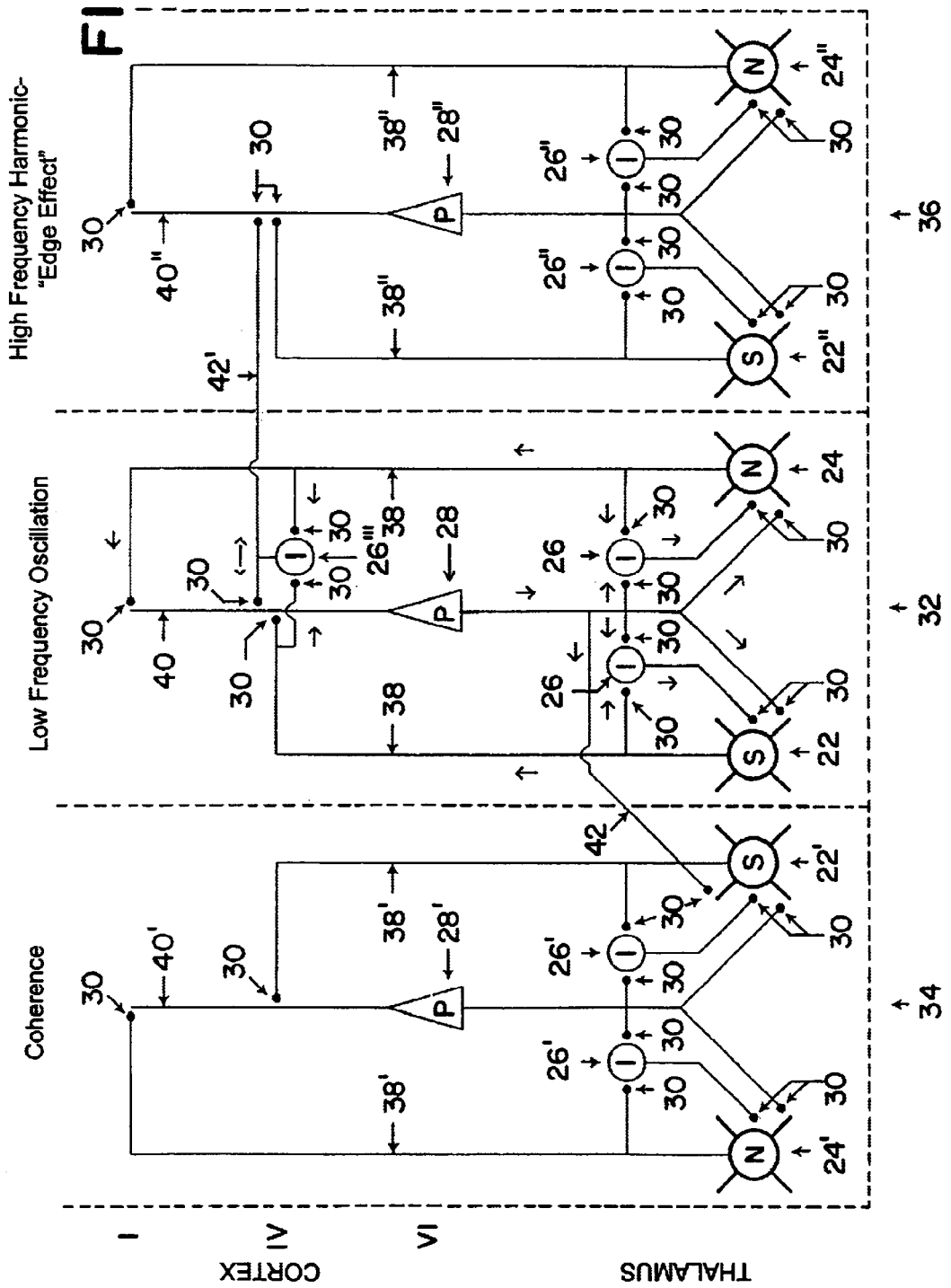

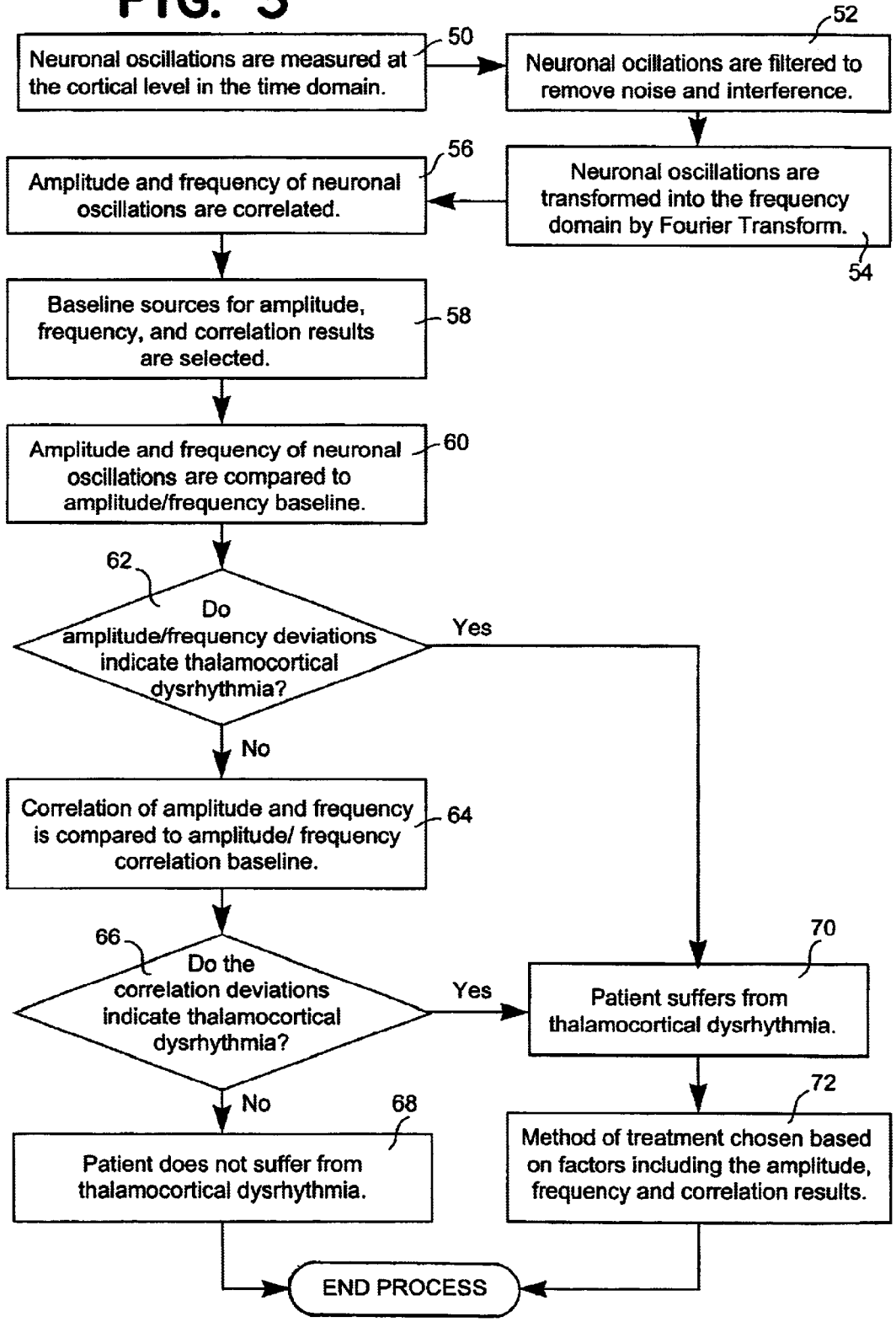

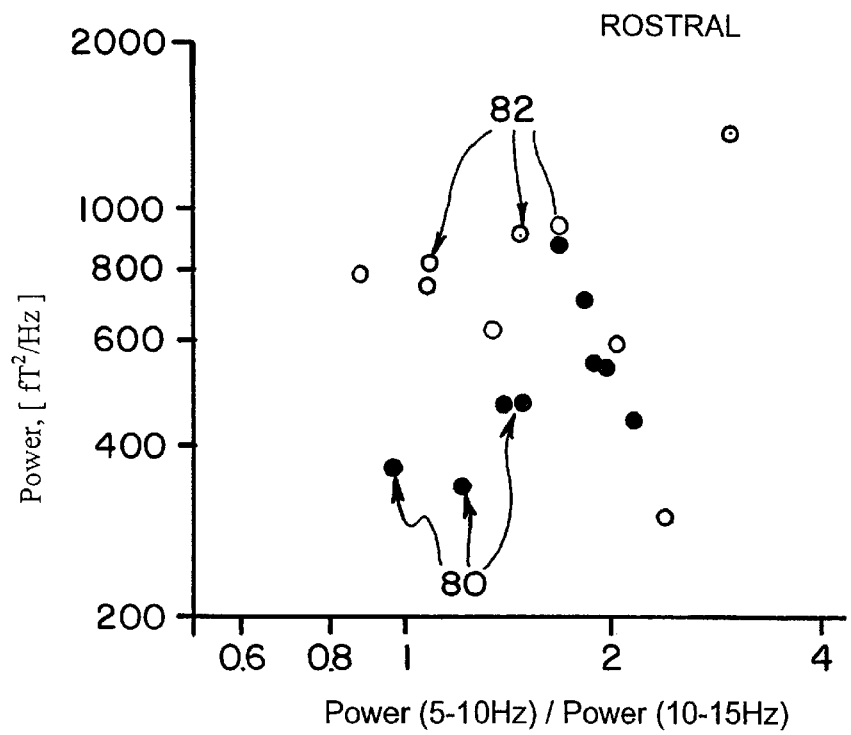
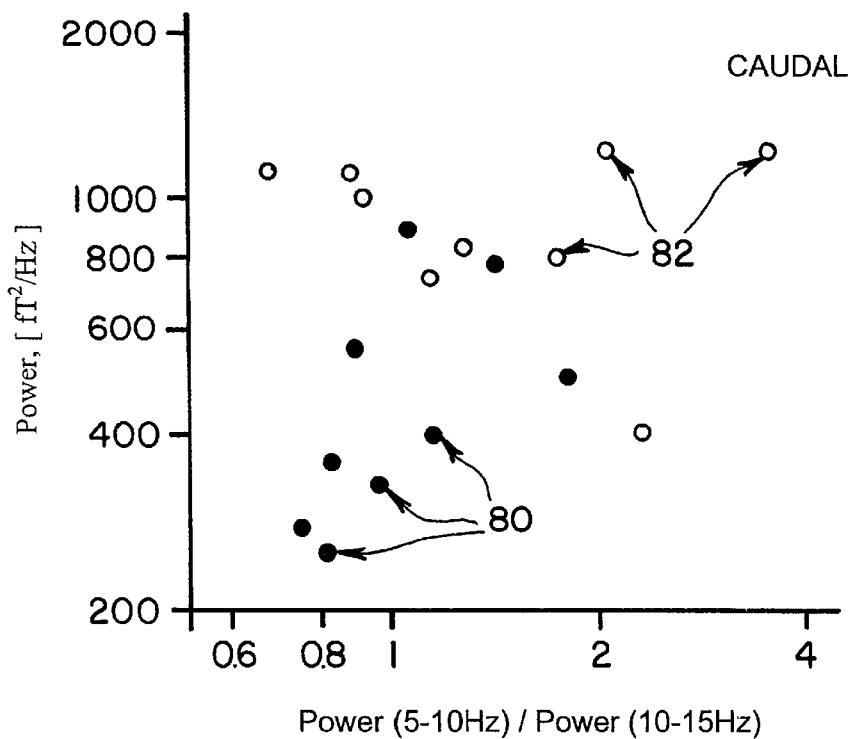

Control

Psychosis

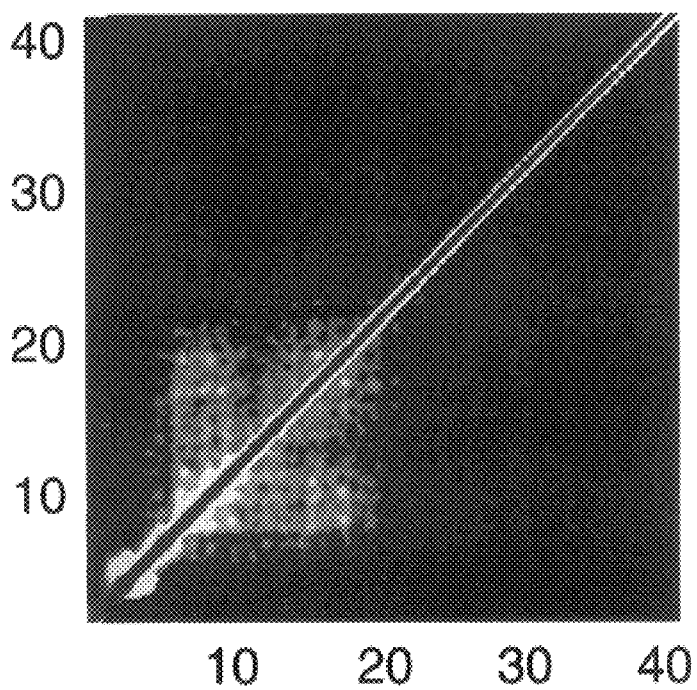
Fig. 9 OCD
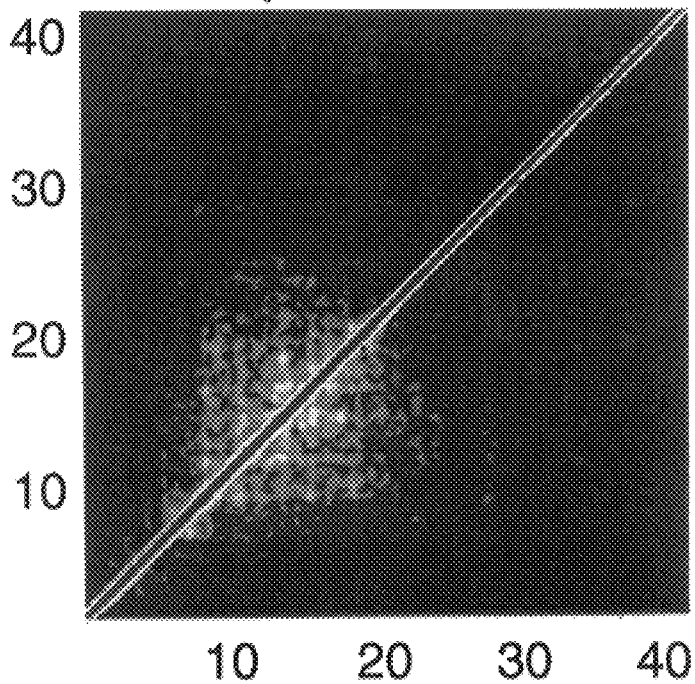
Fig. 10 Depression

Neuropathic Pain

Parkinson's

Tinnitus

Normal Control

Psychosis Eyes Open
(Pre-Surgical)

Psychosis Eyes Closed
(Pre-Surgical)

Psychosis Eyes Closed
(Post-Surgical)

METHOD AND SYSTEM FOR DIAGNOSING AND TREATING THALAMOCORTICAL DYSRHYTHMIA

RELATED APPLICATIONS

This application is based on and claims the priority of Provisional Application Ser. No. 60/210,040, filed Jun. 7, 2000, the contents of which are hereby incorporated herein by reference.

FIELD OF THE INVENTION

The present invention generally relates to the diagnosis and treatment of neurological and neuropsychiatric diseases. More specifically, this invention relates to the diagnosis and treatment of neurological and neuropsychiatric diseases using electromagnetic and frequency analysis techniques.

BACKGROUND OF THE INVENTION

The major theory of motor and cognitive functions hypothesizes that motor and cognitive functions arise from coordinate electrical activity at the cortical level of the brain. Coordinate electrical activity refers to controlled electrical discharges within the brain at both cellular and macrocellular levels. Controlled electrical discharges facilitate communication within and among different regions of the cortex, and thus coordinate electrical activity through controlled electrical discharges at the cortical level of the brain gives rise to motor and cognitive abilities.

At the cellular level, neurons within the brain interact and communicate through electrical signals that are sent between neurons. Neurons send electrical signals via an electrochemical process, wherein an exchange of ions occurs through a neuron's membrane, thereby causing an electrical discharge. When a neuron is in its rest state, the neuron accumulates and maintains a negative charge within its membrane, thereby polarizing a negative potential (typically −70 mV) between the inside and outside of the neuron. The neuron discharges when a stimulus event increases the negative membrane potential beyond a certain threshold value (typically −55 mV), thereby triggering an exchange of ions across the neuron's membrane and depolarizing the neuron. The depolarization and exchange of ions causes a positive discharge, also known as a "spike" or "impulse," that peaks at a net positive potential (typically +30 mV). This positive discharge is sent from the neuron through its axon(s) to the dendrites of recipient neurons, which receive the electrical signal. After the positive discharge, the transmitting neuron returns to its rest state, thereby completing the discharge cycle.

The stimulus event that causes the discharge of a transmitter neuron may occur because of the effect of an inhibitor neuron on the transmitter neuron. An inhibitor neuron acts to prevent the discharge of other neurons, and thus provides a negative feedback mechanism that prevents the discharge of these neurons by maintaining a negative membrane potential. When the inhibitor neuron is itself inhibited, however, then its negative feedback becomes positive, thereby raising the membrane potential to the threshold level and causing those neurons it had been inhibiting to discharge. Thus, inhibitor neurons control the electrical discharge of other neurons.

Stimulus events that affect the discharge of a transmitter neuron may also occur independently of an inhibitor neuron. In particular, the sensory input received by a transmitter neuron may control the discharge of the transmitter neuron. Thus, the general chemical and physiological components around the neuron themselves affect the discharge of a neuron irrespective of inhibitor neurons. As a result, neurotransmitters and other chemical and physiological components may influence the discharge of a neuron.

At the macrocellular level, different regions of the brain are responsible for different cognitive and motor functions. Different layers of the cortex, which is the outer layer of the brain, control different cognitive and motor skills including speech, hearing, sight, touch, smell and thought. The cortex itself has six main cellular levels of neurons (levels I–VI) wherein intracellular communication takes place via electrical impulses. Thus, normal cognitive and motor functions are the product of coordinate electrical activity that occurs at the cortical level.

Also at the macrocellular level, the thalamus resides within the center of the brain and acts as a "communications hub" between different regions of the brain, including the cortex. The normal electrical activity of the thalamus is also coherent, in the sense that the thalamus fires electrical impulses at specific intervals and in a controlled fashion. A plurality of neurons exist between the thalamus and the cortex, thereby creating corticothalamic pathways that facilitate communication and interaction between the thalamus and the cortex.

The thalamus itself is divided into regions that include the sensory thalamus and the reticular nucleus. The sensory thalamus is stimulated by signals from other sensory inputs from the body and communicates those inputs to the cortex. The reticular nucleus surrounds the sensory thalamus and acts to suppress the sensory thalamus from transmitting signals at certain times, such as sleep, when the cortex is to be desensitized from communication with the rest of the body. Thus, the reticular nucleus suppresses the electrical activity and discharge of the sensory thalamus.

The thalamus and the cortex are connected through specific and nonspecific corticothalamic pathways. Specific pathways refer to pathways between the thalamus and particular sensory or motor input regions of the cortex, typically connecting at layer IV of the cortex. Nonspecific pathways refer to pathways between the thalamus and non-sensory and non-motor input regions of the cortex, typically connecting at layers I, IV and V of the cortex. Afferent corticothalamic pathways communicate signals from the thalamus to the cortex, whereas efferent corticothalamic pathways communicate signals from the cortex to the thalamus, thereby closing the communication loop between the cortex and the thalamus.

Coordinate electrical activity is characterized by normal neuronal oscillation (i.e., normal frequencies of electrical oscillation by neurons and neuronic regions), wherein neurons and neuronic regions of the brain discharge electrical impulses at particular frequencies, thereby causing electrical oscillation. At the cellular level, inhibitors and neuronal inputs properly control the chemical release of neurons and thereby facilitate normal electrical discharges by the neurons. At the macrocellular level, the interaction and communication between properly discharging neurons causes normal, coordinate electrical activity characterized by electrical oscillation at different frequencies between and among particular regions of the brain.

Neuronal oscillation generally occurs in a plurality of distinct frequency bands. These frequency bands include the theta (θ) band, which includes low frequency oscillations in the 4–8 Hz range, and are most commonly associated with the four-phase sleep cycle of human beings. These frequency bands also include the gamma (γ) band, which includes high frequency oscillations in the 20–50 Hz range, and which are associated with sensorimotor and cognitive functions. Individuals experience specific types and amounts of theta- and gamma-band activity based on factors including their mental activity level and physical state. For instance, a person who is asleep will typically experience the four-phase theta-band oscillation cycle associated with sleep, whereas a person who is awake and active will experience gamma-band oscillation at the cortical level to perform cognitive and motor functions.

Neuropsychiatric diseases occur when the coordinate, controlled electrical activity at the cortical level of the brain becomes disrupted, thereby leading to uncoordinated electrical activity and abnormal neuronal oscillation. Neuropsychiatric diseases include but are not limited to neurogenic pain, obsessive-compulsive disorder, depression, panic disorder, Parkinson's disease, schizophrenia, rigidity, dystonia, tinnitus and epilepsy. In particular, these and other neuropsychiatric diseases are characterized by thalamocortical dysrhythmia, wherein the electrical oscillation levels and frequencies for different portions of the cortex and thalamus deviate from the oscillation levels and frequencies that exist for persons who do not suffer from neuropsychiatric diseases. Such deviations occur at both the cellular and macrocellular level, and these deviations interfere with the communication among and between different regions of the brain. When this interference occurs in specific regions of the cortex, the interference impairs the motor and cognitive skills that are controlled by those regions of the cortex. This interference manifests itself in the positive symptoms of neuropsychiatric disease that are caused by the interference that occurs in different cortical regions.

It has been generally known that normal neuronal oscillation is characterized by neuronal activity at certain frequencies for certain neurological diseases. In addition, numerous invasive and non-invasive methods of measuring the neuronal oscillation at the cortical level are known, including electroencephalography (EEG), magnetoencephalography (MEG). Thus, certain conventional methods are able to determine the presence or absence of neuropsychological diseases based on measurements of neuronal oscillation at the cortical level.

None of these known methods describes the precise nature of neuronal oscillations, including their characteristics and degree of deviation from normal neuronal oscillation patterns. In fact, none of the known methods disclose what characterizes a suitable baseline of normal neuronal oscillation, what is considered a deviation from a suitable baseline of normal neuronal oscillation, and most important, what mechanism causes deviations from the baseline of normal neuronal oscillation that causes neuropsychiatric disease. Thus, although known methods describe the general and unremarkable principles of neuronal oscillation and use of neuronal oscillation measurements as a basis to diagnose and treat neuropsychiatric diseases, none of these methods describe or disclose precisely how to diagnose neuropsychiatric diseases that are caused by thalamocortical dysrhythmia. Without the ability to describe the nature of normal neuronal oscillation and the significance of deviations from normal neuronal oscillation, the ability to diagnose a patient who may suffer from neuropsychiatric diseases caused by thalamocortical dysrhythmia through measurement of the patient's neuronal oscillation is at the least incomplete, and at the best ineffective.

SUMMARY OF THE INVENTION

These and other deficiencies in the prior art are addressed by the present invention, which is a method and system for diagnosing and treating thalamocortical dysrhythmia. In particular, the present invention describes the mechanisms that cause thalamocortical dysrhythmia, the characteristics of normal neuronal oscillation and the deviations from normal neuronal oscillation that characterize thalamocortical dysrhythmia. The present invention also describes a method for diagnosis and treatment of thalamocortical dysrhythmia based on these mechanisms, characteristics, and deviations. Thus, the present invention describes a method to measure, record and process electrical activity in the brain, and more specifically the cortex, to diagnose thalamocortical dysrhythmia and prescribe a treatment.

At the cellular level, neuronal cells have individual properties and characteristics within the general neuronal system. Thus, specific neuronal cells are constructed to operate at specific frequencies during different times. When operating nominally, thalamic cells oscillate in the gamma range, typically at 40 Hz, while in the "awake" or active state, and oscillate in the theta range, typically at 4 Hz, while in the "asleep" or inactive state.

Thalamocortical dysrhythmia occurs within the thalamus when thalamic neurons that should be in the active state become imbalanced or hyperpolarized and enter the inactive state while an individual is awake. When such an imbalance takes place, the thalamic cells enter an abnormal "asleep" state wherein they fail to communicate information properly to the cortex through the corticothalamic pathways. This causes the cortex itself to become imbalanced, thereby disrupting coherent electrical activity at the cortical level and causing thalamocortical dysrhythmia.

The change of thalamic neurons from the active to the inactive state may have multiple causes, primarily including overstimulation or under stimulation by inputs to thalamic neurons, and also including excessive inhibition by inhibitor neurons. Thalamic neurons become hyperpolarized, wherein the membrane potential for the neuron's rest state and/or threshold potential changes, as well as changing the actual discharge characteristics of the neuron itself. As a result, the thalamic neurons overcharge and decrease the periodicity of their discharge, which causes abnormally high theta-band oscillation as thalamic neurons send out electrical impulses too late (at a lower frequency) and at a higher amplitude. Thus, within the thalamus, the net result is a shift in neuronal oscillation to lower frequencies and an increased amplitude.

Temporal coherence of these theta-band oscillations occurs at the thalamic level through the corticothalamic pathway loops between the thalamus and the cortex. The theta-band oscillations propagate to the cortex through afferent corticothalamic pathways, and then return to the thalamus through efferent corticothalamic pathways, thereby feeding the theta-band oscillations back to the thalamus. This causes large scale temporal coherence at the thalamic level, as thalamic neurons become synchronized with the theta-band oscillation. This temporal coherence is further driven at the thalamic level through thalamic pathways between neighboring thalamic neurons, as well as common inputs between and among neighboring thalamic cells that are the source of the theta-band oscillations. Thus, the common effect of the corticothalamic pathways, thalamic-level pathways between neighboring thalamic cells, and common thalamic inputs is large scale, theta-band oscillation in the thalamic level, typically at 4 Hz.

Temporal coherence of theta-band oscillations also occurs at the cortical level through the afferent corticothalamic pathways. The theta-band oscillations travel through the afferent corticothalamic pathways to corresponding cortical level neurons, which are linked to the thalamic level neurons as part of a single corticothalamic module. Thus, cortical level neurons become synchronized with their corresponding thalamic neurons in theta-band oscillation, thereby providing temporal coherence between the thalamic and cortical neurons within a single corticothalamic module.

The prevalence and amplitude of gamma-band oscillations at the cortical level also increase from the thalamic interaction with cortical inhibitory neurons. Specifically, afferent specific corticothalamic pathways connect thalamic neurons to cortical inhibitory neurons. The decreased frequency of the theta-band oscillation from thalamic neurons reduces the lateral inhibition of the cortical inhibitory neurons, thereby deinhibiting otherwise normal cortical neurons. This loss of inhibition allows these cortical neurons to increase their high frequency oscillations, thereby causing abnormally high gamma-band oscillation within the cortex. This gamma-band oscillation is temporally coherent with the theta-band oscillation, as the temporally coherent theta-band oscillation is the cause of the gamma-band oscillation. In particular, unlike a normal individual, there is a simultaneous presentation of both theta-band and gamma-band oscillation within the cortex. Thus, an abnormal correlation exists between the increased theta-band and gamma-band oscillation. In other words, whereas normally there is little correlation between theta- and gamma-band oscillation, in an abnormal condition such correlation arises from the simultaneous presence of theta- and gamma-band oscillation, and such abnormal correlation is characteristic of thalamocortical dysrhythmia.

The abnormal temporal coherence and correlation between theta- and gamma-band frequencies, as well as within the theta-band itself, is significant because normal individuals that do not suffer from thalamocortical dysrhythmia may experience a low amount of theta-band oscillation when they are awake and active. For instance, some theta-band neuronal oscillations have been observed, particularly in the rostral pole area, for individuals that are awake and who do not have thalamocortical dysrhythmia. Thus, the mere presence of theta-band neuronal oscillations at the cortical level may be insufficient to diagnose an individual as having thalamocortical dysrhythmia. However, the theta-band neuronal oscillations that sometimes occur in individuals without thalamocortical dysrhythmia are not temporally coherent or correlated as are the theta-band neuronal oscillations for individuals with thalamocortical dysrhythmia. Therefore, the temporal coherence and abnormal correlation of theta-band neuronal oscillations act to distinguish theta-band neuronal oscillations of individuals with thalamocortical dysrhythmia, and theta-band neuronal oscillations of individuals without thalamocortical dysrhythmia. The present invention uses this temporal coherence and correlation to separate theta-band oscillations caused by thalamocortical dysrhythmia from those that are not caused by thalamocortical dysrhythmia.

At the macrocellular level, these oscillatory deviations interfere with the normal coordinate electrical activity necessary for brain functionality and cause neuropsychiatric disease. The primary characteristics of neuropsychiatric disease therefore include an overall increase in the amplitude of theta- and gamma-band oscillations, an increased correlation and temporal coherence between theta- and gamma-band oscillations, and an overall shift toward theta-band frequencies. In particular, at the cortical level, the increased levels of gamma-band oscillations within and among particular cortical regions interfere with the motor and/or cognitive functions controlled by those regions. For example, oscillatory deviations in the auditory cortex or medial geniculate nucleus may cause tinnitus (ringing of the ears), whereas oscillatory deviations in the cingulate cortex may cause depression.

The ability to measure neuronal rhythmicity provides the ability to diagnose individuals who suffer from neuropsychiatric diseases caused by thalamocortical dysrhythmia. In particular, the ability to measure the neuronal rhythmicity in particular cortical regions and correlate such rhythmicity with the rhythmicity associated with neuropsychiatric diseases allows the diagnosis of neuropsychiatric disease. By analyzing the particular cortical regions, their neuronal oscillation frequencies, their neuronal oscillation amplitudes, and their neuronal oscillation correlations, the present invention may be used to diagnose an individual as suffering from thalamocortical dysrhythmia.

In accordance with the present invention, the electrical activity of a patient's brain is measured at the cortical level. In particular, the present invention may use techniques that include magnetoencephalography (MEG) and electroencephalography (EEG) to measure and record electrical activity for particular cortical regions. A Fourier transform of the electrical data then determines the neuronal rhythmicity, i.e., the electrical oscillation frequencies, of regions of the cortex. The present invention is thereby able to determine the neuronal rhythmicity for both the cortex as a whole, as well as for particular regions of the cortex.

Once the neuronal rhythmicity has been determined, the present invention processes the neuronal rhythmicity data to determine whether the data is characteristic of thalamocortical dysrhythmia. In particular, the present invention determines whether the data demonstrates the presence or indicia of abnormal neuronal rhythmicity that is associated with thalamocortical dysrhythmia and different neuropsychiatric diseases. The present invention processes the neuronal rhythmicity data to determine whether thalamocortical dysrhythmia exists, and then diagnoses the neuropsychiatric disease(s) of the patient based on the presence of thalamocortical dysrhythmia.

The present invention may determine the presence of indicia of abnormal neuronal rhythmicity in a plurality of ways. First, thalamocortical dysrhythmia is characterized by higher overall amplitude of neuronal activity as well as a higher ratio of theta-band oscillations to gamma-band oscillations. Any comparative increase in the amplitude of neuronal activity or frequency shift toward prevalence of theta-band oscillations indicates the presence of thalamocortical dysrhythmia. Such a comparative increase may be relative to the patient himself based on prior data regarding neuronal activity, or may be relative to other standards of normal neuronal activity independent of the individual patient. Thus, the present invention diagnoses that an individual is suffering from thalamocortical dysrhythmia by determining that the amplitude or theta-to-gamma ratio of the individual's neuronal oscillations have notably deviated from a reference baseline of amplitude or theta-to-gamma ratio data.

Second, thalamocortical dysrhythmia is characterized by abnormally high correlation between neuronal oscillation frequencies, such as low frequency theta-band and high frequency gamma-band neuronal oscillations. The present invention is able to correlate the different frequencies of neuronal activity to determine the correlation between theta- and gamma-band neuronal oscillations. Any comparative increase in the correlation between theta- and gamma-band neuronal oscillations indicates the presence of thalamocortical dysrhythmia. Such a comparative increase may be relative to the patient himself based on prior data regarding neuronal activity, or may be relative to other standards of normal neuronal activity independent of the individual patient. Thus, the present invention diagnoses that an individual is suffering from thalamocortical dysrhythmia by determining that the correlation of theta-band to gamma-band neuronal oscillations for the individual has notably deviated from a reference baseline of theta-band to gamma-band oscillation correlation.

The present invention can also determine whether thalamocortical dysrhythmia exists for different, specific cortical regions. In particular, the present invention can identify the cortical area(s) where thalamocortical dysrhythmia is present and the nature of the thalamocortical dysrhythmia, including deviant amplitudes of neuronal oscillation, deviant theta-band to gamma-band oscillation ratios, and deviant theta-band to gamma-band correlation. These identifications are compared with the known cortex regions and the nature of the thalamocortical dysrhythmia, as well as with the patient's symptoms to determine the neuropsychiatric disease(s) that afflict the patient. A doctor or other medical professional is then able to prescribe a course of treatment based both on the general neuropsychiatric disease(s) affecting the patient, as well as the precise area and nature of the thalamocortical dysrhythmia that is the cause of the disease(s). Appropriate methods of treatment may include, but are not limited to, surgical treatments such as cortical ablation, electrical treatments such as implanting electrodes for neural stimulation, and pharmacological treatments.

BRIEF DESCRIPTION OF THE DRAWINGS

The foregoing and other features of the present invention will be more readily apparent from the following detailed description and drawings of illustrative embodiments of the invention in which:

FIGS. 1a–c are diagrams of the cortical and thalamic anatomy;

FIG. 2 is a diagram of the corticothalamic pathway interactions;

FIG. 3 is a block diagram of the Thalamocortical Dysrhythmia Treatment process;

FIGS. 5a–c are graphs of the Power Spectrum Versus Power Ratio of Control Subjects and Patients;

FIG. 9 is a graph of the Power Spectrum Correlation for a Patient with OCD;

FIG. 10 is a graph of the Power Spectrum Correlation for a Patient with Depression;

DETAILED DESCRIPTION OF THE PREFERRED EMBODIMENTS

Figure 4A:
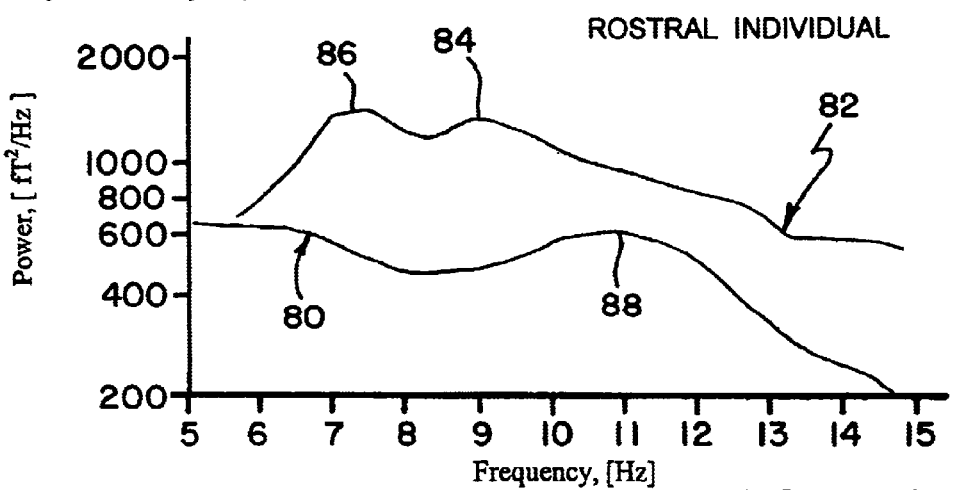
FIGS. 4a–e are graphs of the Power Spectra of Control Subjects and Patients.
Figure 4B:
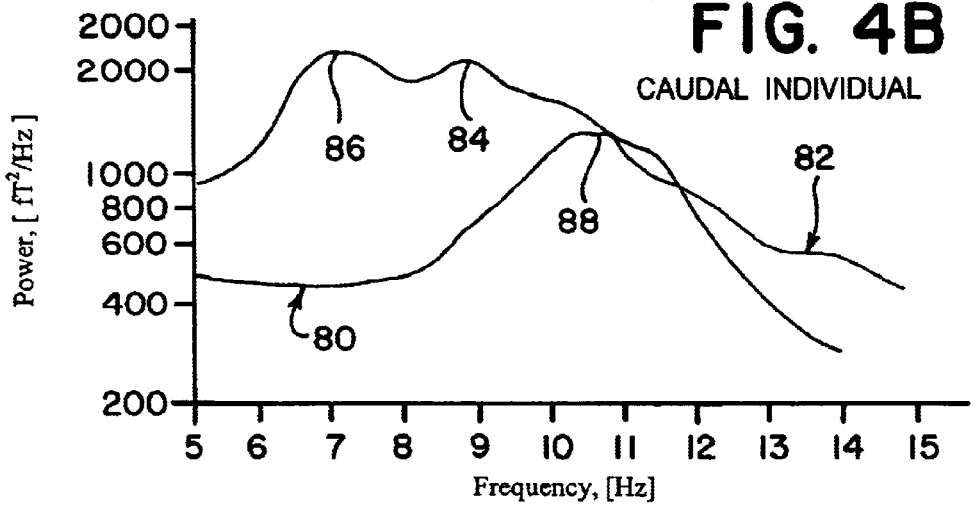

FIGS. 1a–c show a diagram of the cortical and thalamic anatomy, including the location of the thalamus and cortex within the brain, as well as the corticothalamic pathways that connect the cortex and the thalamus. Two views of the brain are shown in FIGS. 1a and 1b. The first view, FIG. 1a, is the sagittal view 16, which is created by a vertical section of the brain that extends from the front to the back of the head as shown in FIG. 1c. The second view, FIG. 11b, is the coronal view 18, which is created by a vertical section of the brain that extends from one side of the head to the other as shown in FIG. 1c.

Turning to FIG. 1a, the cortex 2 resides at the exterior of the brain, and may be subdivided into smaller cortical regions 4. The thalamus 6 resides at the interior of the brain and may also be subdivided into smaller thalamic regions 8. The cortex 2 and thalamus 6 are connected via corticothalamic pathways 10 that carry electrical signals between the cortex 2 and the thalamus 6. Specific cortical regions 4 are connected to their associated thalamic regions 8 through the corticothalamic pathways 10, thereby creating corticothalamic loops between the cortex 2 and the thalamus 6.

FIG. 2 shows the corticothalamic pathway interactions that cause thalamocortical dysrhythmia. In particular, FIG. 2 shows the interactions and feedback between neurons that cause low frequency theta-band oscillation, coherence of this oscillation between thalamic and cortical neurons, and high frequency gamma-band oscillation attributable to the loss of lateral neural inhibition. FIG. 2 shows these interactions as they occur at both the thalamic and cortical levels, within the specific cortical layers, and within separate corticothalamic modules that include distinct corticothalamic loops.

Referring now to FIG. 2, specific nuclei 22, 22' and 22" reside at the thalamic layer and connect to the cortex at layer IV and the cortical pyramidal cells 28, 28' and 28", respectively, that reside in the cortex at layer VI. Nonspecific nuclei 24, 24' and 24" reside at the thalamic level but connect to the cortex at layer I, and also connect to the cortical pyramidal cells 28, 28' and 28", respectively, that reside in the cortex at layer VI. The pyramidal cells 28, 28' and 28" receive signals from the specific nuclei 22, 22' and 22", respectively, and the nonspecific nuclei 24, 24' and 24", respectively, through the afferent corticothalamic paths 38, 38' and 38", respectively, that transmit electrical signals from the thalamus to the cortex. The pyramidal cells 28, 28' and 28" transmit electrical signals to the thalamus through the efferent corticothalamic paths 40, 40' and 40", respectively, from the cortex back to the thalamus. The signals from the efferent corticothalamic paths 40, 40' and 40" feedback to the specific nuclei 22, 22' and 22", respectively, nonspecific nuclei 24, 24' and 24", respectively, and inhibitor neurons 26, 26' and 26", respectively, at the thalamic level. Thus, the afferent 38, 38' and 38" and efferent 40, 40' and 40" corticothalamic paths create corticothalamic loops that carry electrical signals from the thalamus to the cortex and then back to the thalamus, and vice versa. The inhibitor neurons 26, 26' and 26" reside at the thalamic level and control the electrical discharge of the specific nuclei 22, 22' and 22", respectively, and nonspecific nuclei 24, 24' and 24", respectively. The inhibitor neuron 26''' resides at layer IV of the cortex and acts as a lateral inhibitor of other cortical and thalamic neurons. The synapses 30 mark the signal transition point from the axon of one neuron to the dendrites of another neuron.

Corticothalamic modules 32, 34 and 36 are formed through the combination and interconnection of one specific nucleus, one nonspecific nucleus and one pyramidal cell. For instance, the corticothalamic module 32 includes one specific nucleus 22, one nonspecific nucleus 24, and one pyramidal cell 28. These neurons connect through the afferent and efferent corticothalamic pathways 38 and 40, respectively, which forms a junction between specific and nonspecific corticothalamic loops that causes the neurons to oscillate within the same frequency band. As an example, if the specific and nonspecific nuclei 22 and 24 are in the "active" state and oscillating within the gamma-band at approximately 40 Hz, then the pyramidal cell 28 will also oscillate within the gamma-band at approximately 40 Hz. Similarly, if the specific and nonspecific nuclei 22 and 24 become unbalanced and enter the "inactive" state, wherein they oscillate within the theta-band at approximately 4 Hz, then the pyramidal cell 28 will also oscillate within the theta-band at a frequency of approximately 2–8 Hz.

In normal operation, thalamocortical modules 32, 34 and 36 are all in an active state of oscillation in the gamma-band when an individual is awake. The feedback within the thalamocortical modules 32, 34 and 36, as well as between the thalamocortical modules 32, 34 and 36, maintains gamma-band oscillation at approximately 40 Hz. Thus, there is little indicia of theta-band oscillation and there is no temporal coherence between gamma-band oscillation and whatever theta-band oscillation exists. In other words, there is little theta-band oscillation, and what theta-band oscillation that exists is not correlated with the more prevalent gamma-band oscillation.

Thalamocortical dysrhythmia occurs when abnormal theta-band oscillation occurs within the thalamic nuclei of a corticothalamic module for an individual that is awake. The corticothalamic module 32 shows the interactions that cause such theta-band oscillations. In the corticothalamic module 32, the specific nuclei 22 and nonspecific nuclei 24 enter a state of hyperpolarization. As a result of the hyperpolarization, the nuclei 22 and 24 discharge their electrical impulses too late and at a higher amplitude than normal to cause theta-band oscillation. These electrical impulses travel along the afferent corticothalamic pathways 38 to the cortical level, and down the efferent corticothalamic pathway 40 to the pyramidal cell 28. The pyramidal cell 28 discharges its own electrical impulse, which travels back to the thalamic level through the efferent pathway 40 to the specific nucleus 22, nonspecific nucleus 24 and inhibitor neurons 26. The return signal by the pyramidal cell 28 closes the corticothalamic loop and reinforces the hyperpolarization. The conjunction of the specific and nonspecific loops formed by the afferent 38 and efferent 40 corticothalamic paths causes temporal coherence of the theta-band oscillation between the specific nucleus 22, nonspecific nucleus 24 and pyramidal cell 28.

The theta-band oscillation propagates to other corticothalamic modules 34 through the feed forward effects of the thalamic level lateral paths 42 between the corticothalamic module 32 experiencing theta-band oscillation and its neighboring corticothalamic modules 34. In addition, the neighboring corticothalamic module 34 may also experience the same stimulus that caused the hyperpolarization of the first corticothalamic module 32, thereby causing temporal coherence between the corticothalamic modules 32 and 34. The lateral path 42 at the thalamic level reinforces the theta-band oscillation of the neighboring corticothalamic module 34, which is presented at the cortical level through the afferent 38' corticothalamic pathway to the pyramidal cell 28'. Thus, the specific nucleus 22', nonspecific nucleus 24', and pyramidal cell 26' engage in coherent theta-band oscillation that is correlated with the neighboring corticothalamic module 32.

In addition, the theta-band oscillation in corticothalamic module 32 also causes gamma-band oscillation in neighboring corticothalamic modules 36 through the loss of lateral inhibition at the cortical level. The inhibition of the cortical inhibitor neuron 26''' is reduced by the theta-band oscillation from the thalamic level that reaches the inhibitor neuron 26''' via the afferent corticothalamic paths 38. The inhibitor neuron 26''' reduces its inhibition of the pyramidal cell 28'' in the neighboring corticothalamic module 36, which increases its frequency of activity due to the loss of inhibition. Thus, neighboring corticothalamic modules 36 experience high frequency gamma-band oscillations. These gamma-band oscillations feed to the specific nucleus 22'', nonspecific nucleus 24'' and inhibitor neurons 26''' through the efferent corticothalamic paths 40'', which reinforce the gamma-band oscillation by the return afferent corticothalamic paths 38''. In addition, the gamma-band oscillation of corticothalamic module 36 and the theta-band oscillation of the corticothalamic module 32 are temporally coherent and correlated because the theta-band oscillation drives the gamma-band oscillation. Thus, the gamma- and theta-band oscillations are temporally coherent and correlated at both the cortical and thalamic levels.

At the macrocellular level, the interactions between the corticothalamic modules 32, 34 and 36, as well as other similarly affected modules, causes thalamocortical dysrhythmia. In particular, two distinct types of interrelated activity are present and may be detected at the cortical level. The first is the coherent theta-band oscillation present between and within a plurality of corticothalamic modules 32 and 34, and the second is the coherent gamma-band oscillation present between and within a plurality of additional corticothalamic modules 36. In addition, the theta- and gamma-band oscillations of all corticothalamic modules 32, 34 and 36 are temporally correlated, in that they exist nearly simultaneously within a single region of the brain.

The practical effect of the corticothalamic module interactions is that a plurality of corticothalamic modules 32 and 34 enter an inactive state where they are unable to process information, thereby leading to a loss of cognition or motor skills. This is primarily caused by the defective input into the specific nuclei 22 and 22' and nonspecific nuclei 24 and 24', which are either overstimulated or under stimulated by the defective input. This changes the fundamental oscillation frequency of the specific nuclei 22 and 22' and nonspecific nuclei 24 and 24', which creates a defect within the neuronal network. These defects propagate through the neuronal network to the cortical level, at which the properties of both individual cortical neurons and the network itself are further changed in an abnormal fashion. The sum effect is an unbalanced neuronal network caused by the defective input at the thalamic level and propagated to other neuronal cells through the corticothalamic pathways.

In addition to the inactive state experienced by some corticothalamic modules 32 and 34, other corticothalamic modules 36 experience a state hyperactivity, wherein there is an overload of cognition or motor skills. Caused by a reduction of lateral inhibition, the otherwise normal corticothalamic modules 36 increase their level of activity and thereby change their frequency characteristics. In particular, unlike the inactive corticothalamic modules 32 and 34, the corticothalamic modules 36 that enter hyperactivity does not have defective input at the thalamic level that causes the corticothalamic module to enter a state of inactivity. Instead, the loss of lateral inhibition from the cortical inhibitor neuron 26" causes an increased state of activity and increased gamma-frequency activity.

The colocation of inactive corticothalamic modules 32 and 34, and hyperactive corticothalamic modules 36, generates the "edge effect" caused by adjacent regions of inactivity and hyperactivity in the cortex. In particular, one or more inactive regions that include inactive corticothalamic modules 32 and 34 is located adjacent to one or more hyperactive regions that include hyperactive corticothalamic modules 36, thereby causing a loss of cognition or motor skills for the inactive region while also causing over cognition and inability to control motor skills in the hyperactive region. Thus, the colocation of inactive and hyperactive regions creates an "edge" between inactivity and hyperactivity, both of which disrupt motor and cognitive skills.

The edge effect manifests itself in physiological symptoms based on the particular region effected. For instance, individuals that suffer migraine headaches and experience the edge effect commonly report seeing a visual image of a bright halo surrounding a black spot. This occurs because the edge effect takes place in the visual cortex, and thus the black spot corresponds to a circular inactive region wherein no visual processing occurs, whereas the bright ring corresponds to the hyperactive region that is adjacent to the circular inactive region and surrounds the inactive region in the form of a ring. Similarly, the ringing in the ears experienced by tinnitus patients is due to the hyperactive regions of cells in the auditory cortex that over process information even where there is no auditory input, and the loss of motor control by Parkinson's patients is due to the hyperactive region of cells in motor regions of the cortex that cause involuntary movement.

The root cause of the loss of cognition and motor skills as manifested in the edge effect remains the inactive thalamic cells. The defective thalamic cells can be identified based on their relationship with the corresponding cortical cells, however, and therefore can be treated if the defective cortical cells can be identified. The characteristics of the defective cortical cells, and more particularly their neuronal activity, include a frequency shift towards the theta-band for oscillation, an increase in overall oscillation amplitude, and most distinctively, an abnormal correlation between theta-band and gamma-band oscillation. The present invention uses these characteristics to diagnose and treat a patient for thalamocortical dysrhythmia.

FIG. 3 shows the Thalamocortical Dysrhythmia Treatment process, wherein thalamocortical dysrhythmia is measured, identified, diagnosed and treated based on electromagnetic measurements of the brain, and in particular, the cortex of the brain. The diagnosis process shown may be applied to diagnose both general thalamocortical dysrhythmia, as well as specific subsets of thalamocortical dysrhythmia that cause different neuropsychiatric diseases. Thus, the measurements and baselines chosen in the treatment process may be those appropriate for a general diagnosis, or may be tailored for particular symptoms and neuropsychiatric diseases including neurogenic pain, obsessive-compulsive disorder, depression, panic disorder, Parkinson's disease, schizophrenia, rigidity, dystonia, tinnitus and epilepsy.

As shown in FIG. 3, the treatment process begins when a patient's neuronal oscillations are measured at the cortical level in real time (step 50). Apparatuses used to measure the neuronal oscillations include magnetoencephalography (MEG), which measures neuronal oscillations by detecting the magnetic flux caused by electrical impulses in the brain. Once the neuronal oscillations have been measured in step 50, the remaining steps may occur in real time, or the neuronal oscillation data may be stored with application of the remaining steps at a later time.

After measurement, the neuronal oscillation data is filtered to remove extraneous noise, such as that caused by the heart, thereby leaving only measurements of the cortex's electrical activity (step 52). The neuronal oscillation data is then transformed into the frequency domain using a Fourier transform (step 54). The frequency domain neuronal oscillation data is further correlated to generate frequency—frequency correlation results (step 56). Such frequency—frequency correlation calculates the correlation, and hence temporal coherence, of neuronal oscillations throughout the measured frequency spectrum, and thereby include the correlation of theta-band oscillation to gamma-band oscillation that indicates the presence or absence of thalamocortical dysrhythmia.

Once the frequency, amplitude and frequency correlation data has been determined from the neuronal oscillation measurements, one or more appropriate measurement baselines are then selected to compare with the frequency, amplitude and correlation data (step 58). Appropriate measurement baselines include, but are not limited to, prior measurements of the same patient, prior measurements of "normal" individuals and groups of individuals that do not suffer from neuropsychiatric disease, prior measurements of other patients and groups of patients with similar and different symptoms of neuropsychiatric disease, and prior measurements from medical studies and other general sources of appropriate measurement baseline information. In particular, the increased correlation between theta- and gamma-band neuronal oscillations is itself a sufficient measurement baseline independent of any particular patient or individual, such that different degrees of frequency correlation are themselves an appropriate measurement baseline for neuronal oscillation correlation data. Measurement baselines provide a reference point for data comparison, wherein the deviation or lack thereof of the frequency, amplitude and correlation data from one or more measurement baselines indicates the presence or absence of thalamocortical dysrhythmia.

After selection of one or more measurement baselines, the measured frequency, amplitude and correlation data is compared with the measurement baselines to determine if the patient suffers from thalamocortical dysrhythmia. First, the non-correlated amplitude and frequency data is compared to the amplitude and frequency baselines to determine the amount of deviation between the baselines and the neuronal oscillation amplitude and frequency data (step 60). It is then determined if the amplitude or frequency deviations or lack thereof indicate the presence or absence of thalamocortical dysrhythmia (step 62). For instance, if the amplitude or frequency deviations are similar to patients that suffer from thalamocortical dysrhythmia or notably deviate from individuals that do not suffer from thalamocortical dysrhythmia, then the patient may be diagnosed as suffering from thalamocortical dysrhythmia. In contrast, if the amplitude or frequency deviations are similar to patients that do not suffer from thalamocortical dysrhythmia, then the patient may be diagnosed as not suffering from thalamocortical dysrhythmia.

The amount of deviation from normal or abnormal amplitude or frequency may include an amplitude or frequency threshold that defines normal or abnormal neuronal oscillations. In this embodiment, at least one set of baseline amplitude or frequency data acts as a threshold, and exceeding or dropping below a one or more thresholds may be used as the deviation basis to determine if an individual suffers from thalamocortical dysrhythmia. For instance, one or more amplitude ceiling thresholds can be defined, and if neuronal oscillation measurements exceed the ceiling thresholds in a certain fashion, then the individual is diagnosed as having thalamocortical dysrhythmia. Similarly, floor thresholds may be defined, and neuronal oscillation measurements below the floor thresholds may indicate the individual does not have thalamocortical dysrhythmia. Finally, a plurality of thresholds can be defined for different frequencies, amplitudes and power ratios; when the neuronal oscillation measurements meet or fail to meet certain threshold combinations, then an individual may be diagnosed as having or not having thalamocortical dysrhythmia.

If the patient is diagnosed as suffering from thalamocortical dysrhythmia, then the process proceeds to step 70. If the patient is not diagnosed as suffering from thalamocortical dysrhythmia, then the process proceeds to step 64. In addition, the results at step 62 may be inconclusive, in which case the amplitude and frequency deviation results can be weighed in conjunction with the correlation results at step 66 to determine if an individual has thalamocortical dysrhythmia.

At step 64, the correlated frequency data is compared to the correlated frequency baselines to determine the amount of deviation between the baselines and the neuronal oscillation correlation data. It is then determined if the correlation deviations or lack thereof indicate the presence or absence of thalamocortical dysrhythmia (step 66). For instance, if the correlation data is similar to patients that suffer from thalamocortical dysrhythmia or notably deviates from individuals that do not suffer from thalamocortical dysrhythmia, then the patient may be diagnosed as suffering from thalamocortical dysrhythmia. In contrast, if the correlation data deviates from patients that suffer from thalamocortical dysrhythmia or is similar to patients that do not suffer from thalamocortical dysrhythmia, then the patient may be diagnosed as not suffering from thalamocortical dysrhythmia.

In addition, because the correlation of theta-band and gamma-band neuronal oscillation is itself an indicia of thalamocortical dysrhythmia, the presence of significant theta-band to gamma-band correlation is itself sufficient to make a diagnosis of thalamocortical dysrhythmia. In other words, a default measurement baseline for correlation data that is always available and may be selected at step 58 is the non-correlation of theta-band and gamma-band oscillation in individuals that do not suffer from thalamocortical dysrhythmia. When comparison against this baseline is performed at step 64, then the presence of significantly increased theta-to-gamma band correlation at step 66 is sufficient to diagnose the individual as suffering from thalamocortical dysrhythmia.

Furthermore, correlation baselines may also be used as a measurement threshold at step 66 just as reference amplitude and frequency baselines may be used as a measurement threshold in step 62. Thus, one or more correlation thresholds, ceilings and floors may be established and selected as the baseline in step 58. Certain combinations of correlation measurements that exceed or fall below these thresholds may then be used to determine if an individual has thalamocortical dysrhythmia.

At step 66, if the patient is diagnosed as suffering from thalamocortical dysrhythmia, then the process proceeds to step 70. If the patient is not diagnosed as suffering from thalamocortical dysrhythmia, then the process proceeds to step 68, and the patient does not suffer from thalamocortical dysrhythmia. It should be noted that the diagnosis performed at steps 62 or 66 may themselves be independently conclusive such that the process proceeds to step 70; however, the results of steps 62 and 66 may be such that, when weighed together, they are sufficient to determine the absence or presence of thalamocortical dysrhythmia, thereby proceeding to steps 68 or 70, respectively.

At step 70, the patient has been diagnosed as suffering from thalamocortical dysrhythmia, and thus the process proceeds to step 72, where an appropriate treatment method is selected. An appropriate treatment is chosen based on information including the frequency, amplitude and correlation data, as well as their comparisons to the baseline measurements. Appropriate treatments may include surgery, electrical stimulation, or pharmacological treatment.

The neuronal oscillation measurements shown in step 50 include the use of any measurement technique sufficient to measure the electrical activity for different regions of the cortex of the brain. One embodiment of the present invention uses magnetoencephalography (MEG) to measure neuronal oscillations as stated in step 50. MEG uses Superconducting Quantum Interference Devices (SQUID) to measure the magnetic flux produced by the cortex at different regions using a plurality of probes. Referring again to FIG. 1, the probes 14 are shown as surrounding the cortex 2, and are used to determine the electrical activity in particular cortical regions 4. Each probe 14 measures the magnetic flux produced by the cortex 2; in particular, the electrical activity of a specific cortical region 4 can be determined based on the measurements of a plurality of probes 14, thereby allowing the determination of neuronal oscillation for particular cortical regions 4.

Referring back to FIG. 3, the measurement time necessary to determine the electrical activity of the cortex is merely that length of time necessary to provide a sufficient sample of electrical activity to make a diagnosis. In one embodiment of the present invention, a patient is measured for 10 minutes using a sample rate of 1,000 Hz; in another embodiment of the present invention, measurements are taken for 5 minutes at a sample rate of 1,000 Hz.

According to FIG. 3, the neuronal oscillation filtering that occurs in step 52 is necessary to remove other electrical noise, or artifacts, that interfere with measurement of cortical activity. In particular, cardiac artifacts (electrical activity of the heart) are filtered by taking EKG measurements at the measurement step 50, measuring the cardiac spike times (peak electrical activity of the heart), extracting interpolated cardiac spike shapes which are validated using multitaper cross-coherence with the EKG time series, and subtracting the spike shapes from the measurement data in the frequency domain. In addition to cardiac artifacts, other sources of noise are also filtered by performing a moving average on the neuronal oscillation data using a moving average window.

The Fourier transform of the neuronal oscillations shown in step 54 may be performed using any appropriate Fourier transform method, including Fast Fourier Transform (FFT), or as the preferred method, a tapered Fourier transform using Slepian sequences. Slepian sequences are a set of orthogonal basis functions wk(t) defined on the time interval $t=1, 2 \ldots T$, with a bandwidth parameter "W." By definition, there are $K=2WT$ basis functions, with a spectra confined to a frequency band $[f-W, f+W]$ around a frequency of interest "f."

For a given data sequence x(t), which for the present invention is the neuronal oscillation data, the tapered Fourier transform is given by the following:

$$\tilde{x}_k(f) = \sum_t x(t) w_k(t) e^{-2\pi i f t}$$

On this basis, the direct estimate of the neuronal oscillation data's frequency spectrum is given by the following:

$$S_{MT}(f) \approx \frac{1}{K} \sum_{k=1}^{K} |\tilde{x}_k(f)|^2$$

The advantage of using the tapered Fourier transform using Slepian sequences is that the average across the tapers reduces the variance by a factor of (1/K).

The period of time used to create a power spectrum via Fourier transform is merely the length of time necessary to provide a sufficiently accurate determination of the power spectrum of cortical electrical activity. For general purposes, the Fourier transform of the entire neuronal oscillation data sequence x(t) may be performed to create the frequency spectrum of all neuronal oscillation data. Thus, for embodiments wherein samples are taken at 1,000 Hz for 5–10 minutes, the entire data sequence for the 5–10 minutes may be used as the source data sequence x(t) for the Fourier transform.

The results of such a Fourier transform for neuronal oscillation data is shown in FIGS. 4a–e, which are graphs of the Power Spectra of Control Subjects and Patients. In particular, FIGS. 4a–e plot the power (i.e., amplitude) of the neuronal oscillation data versus the frequency of the neuronal oscillation. FIGS. 4a–e show this information for both control subjects that exhibit normal neuronal oscillation patterns as well as patients that exhibit thalamocortical dysrhythmia. The information is also shown for the whole head, as well as for the rostral and caudal regions for both individual patients and control subjects, as well as for the average of groups of patients and control subjects. For the graphs shown, there are nine control subjects and nine patients suffering from various neuropsychiatric diseases caused by thalamocortical dysrhythmia.

Examining FIGS. 4a–e, the control subjects 80 exhibit a peak neuronal oscillation power at approximately 10 Hz (88), thereby peaking well outside the theta-band and exhibiting no signs of thalamocortical dysrhythmia. In contrast, the patients 82 demonstrate both a low frequency shift and an increase in power relative to the control subjects that distinguishes the patients 82 from the control subjects 80. First, the highest frequency peak 84 for the patients 82 exhibits a low frequency shift towards the theta-band, as would be expected when thalamocortical dysrhythmia is present. Second, the control subjects 80 also include a second lower-frequency peak 86 that is clearly within the theta-band, which is also expected when thalamocortical dysrhythmia is present. Third, the control subjects 80 demonstrate an overall increase in spectral power, which is expected based on the loss of inhibition and general increase in overall and theta-band oscillation. Thus, the patients 82 demonstrate a shift to theta-band frequencies and increase in power that may be used to diagnose them as suffering from thalamocortical dysrhythmia.

Figure 5C:
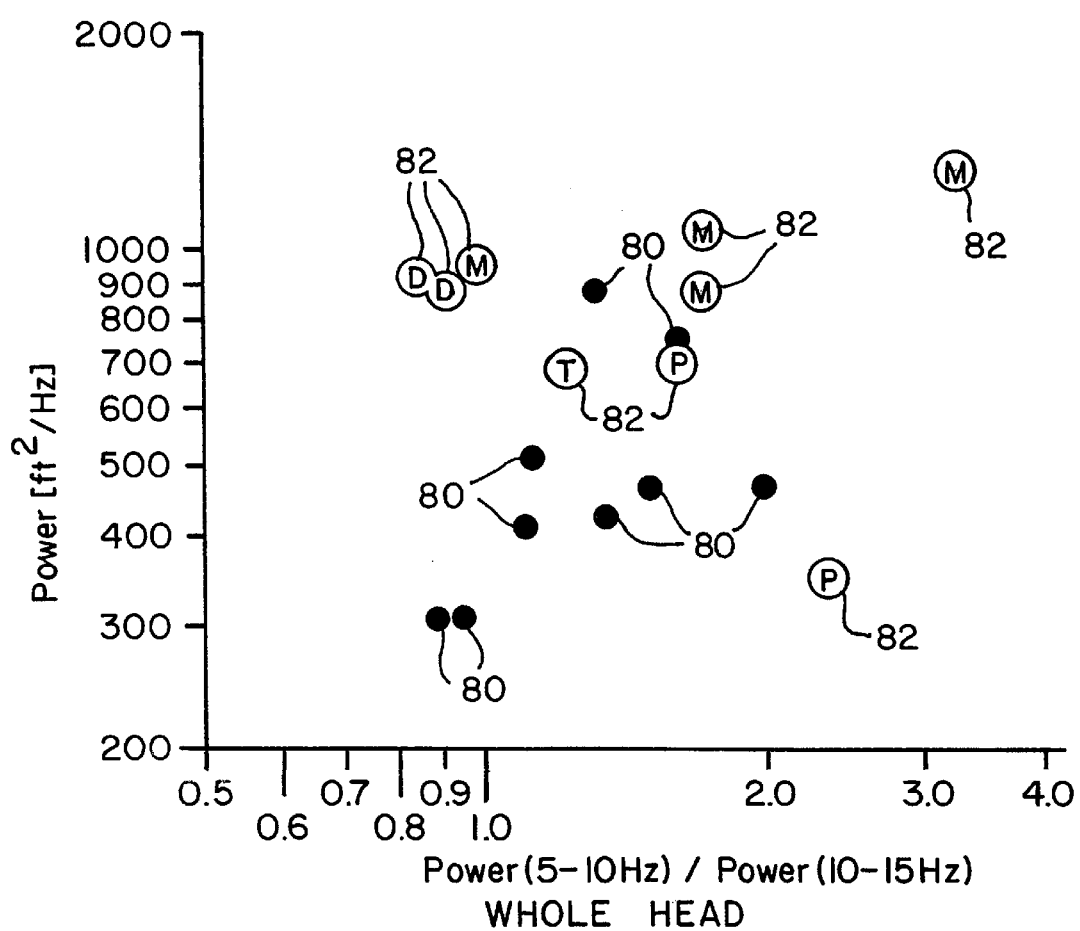

The simultaneous effect of the lower frequency shift and increase in amplitude is shown in FIGS. 5a–c, which are graphs of the Power Spectrum Versus Power Ratio of Control Subjects and Patients. FIGS. 5a–c plot the total power spectra of the control subjects and patients versus the ratio (and hence distribution) of the power spectra from the 5–15 Hz range. In particular, the power ratio plotted on the horizontal axis is the power in the 5–10 Hz range divided by the power in the 10–15 Hz range. In general, it would be expected that this power ratio would be larger for patients suffering from thalamocortical dysrhythmia, because the patients experience a power shift towards the lower frequencies and the theta-band in particular. In regard to the total power spectra, that would be expected to be higher for patients based on the overall increase in neuronal oscillations, particularly in the theta-band. Thus, control subjects would be expected to reside in the lower-left quadrant that corresponds to a lower power ratio and lower total power, whereas patients would be expected to reside in the upper-left, lower-right and upper-right quadrants that correspond to a higher power ratio and increased overall power.

Turning to FIGS. 5a–c, these expectations are affirmed. As qualitatively shown, the control the control subjects 80 tend to reside in the lower left-hand quadrant of the graph that corresponds to low power ratios and low total power. In contrast, the patients 82 tend to surround the control patients by residing in the upper-left, lower-right and upper-right quadrants. Thus, whereas the control subjects 80 tend to cluster towards the origin of the graph, the patients 82 that suffer from thalamocortical dysrhythmia tend to extend away from the origin at the outer axes of the graph.

The increased amplitude and power ratio as shown in FIGS. 4a–e and 5a–c provide the bases for determining if a patient does in fact suffer from thalamocortical dysrhythmia. Thus, the different power ratio, frequency shift and total power measurements provides a qualitative and quantitative baseline from which to determine whether a patient suffers from thalamocortical dysrhythmia. As applied to the treatment process of FIG. 1, the amplitude and frequency baseline sources selected at step 58 may include the frequency shift, power ratio and/or total power measurements from a control subject or patient, average from a group of subjects or patients, or even a comparison with a patient's prior measurements when the patient was symptomatic or asymptomatic (e.g., a patient who went into treatment but then went into remission). Amplitude and frequency baselines may also include any other real or artificial baseline derived from a theoretical or actual basis for determining the power and frequency characteristics of thalamocortical dysrhythmia (e.g., direct modeling of the thalamocortical system itself to derive its characteristics). Once one or more amplitude or frequency baselines have been selected, then the amplitude and frequency deviation calculations and analysis can be performed in steps 60 and 62, respectively, to determine qualitatively or quantitatively whether the patient suffers from thalamocortical dysrhythmia.

The recordings of the patients shown in FIGS. 4a–e and 5a–c are made to determine if a clear grouping could be obtained from MEG measurements in control subjects and in patients. A set of recordings of spontaneous activity is obtained, and the results are analyzed, such that an unbiased plot can be drawn. The recordings obtained from a control subject and patient (FIGS. 4a–b) illustrate the differences in overall frequency content for the rostral and caudal halves of the brain. Note the peak frequencies are clearly different for the control subject 80 and patient 82, with the difference in the in low-frequency activity being most clearly recognizable in the caudal pole shown in FIG. 4b. This result is to be expected, because both sets of recordings were obtained when the subject's eyes were closed. Under these conditions, the alpha rhythm is very prominent in the caudal pole. The results obtained in the patient 82 indicate a shift from a normal alpha rhythm to a robust low-frequency theta rhythmicity. The differences in the rostral pole are less prominent, in agreement with the fact that under certain circumstances, theta rhythmicity is observed in normal individuals. However, the coherence helps to separate "normal" from "abnormal" theta-band frequencies.

Figure 4C:
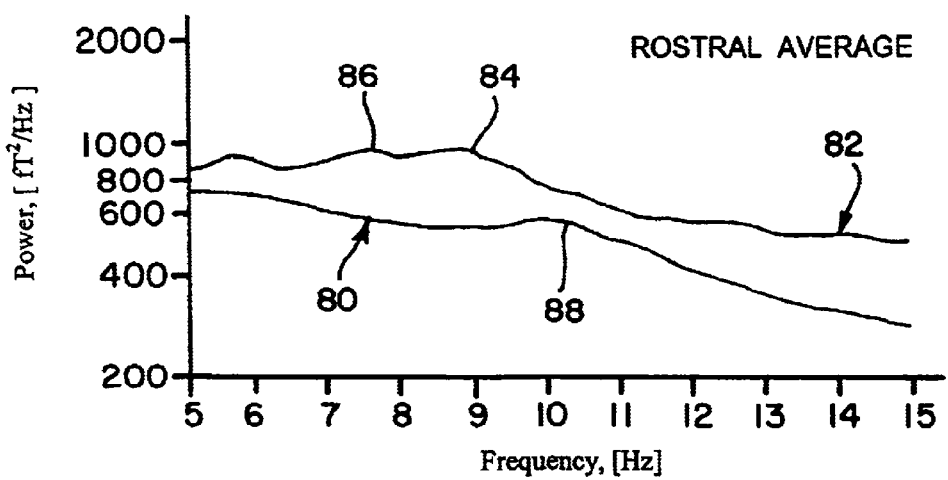
Figure 4D:
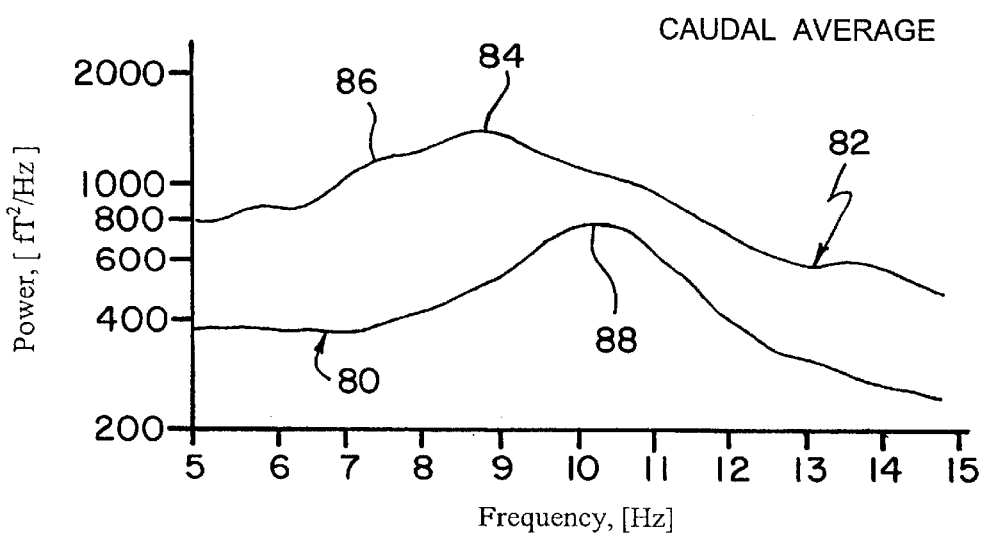
Figure 4E:
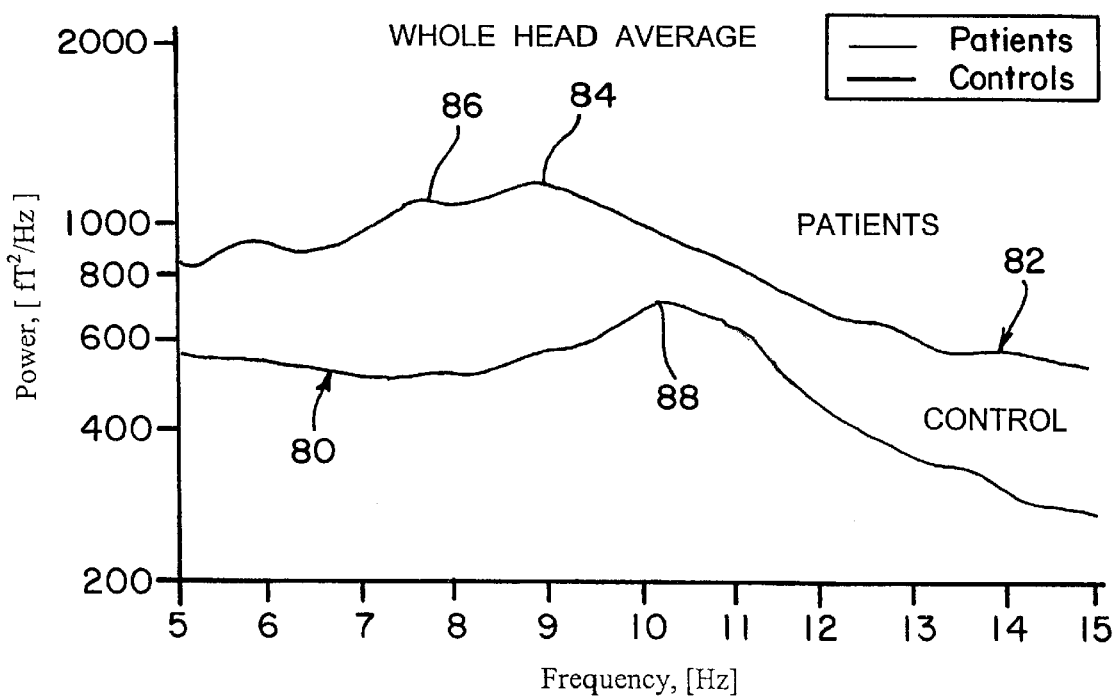

The average power spectra of the recording from a plurality of patients and control subjects are shown in FIG. 4c for the rostral pole, FIG. 4d for the caudal poles, and FIG. 4e for the aggregate of all channels in the control and patient group. Note that the individual recordings in FIGS. 4a–b and the aggregate plot in FIG. 4e illustrate the same characteristics with respect to frequency and rostrocaudal location. Comparing the average power spectra obtained from all of the patients with those obtained from all of the control subjects (FIGS. 4c–e) indicates, once again, a decrease in alpha power and an increase in lower-frequency activity in the theta range, as well as an increase in global power. The latter would be expected if overall coherence had increased in the patient group.

These findings are confirmed by the plots of the total power in the 5–15 Hz band against the power ration between the 5–10 Hz band and between the 10–15 Hz band (FIGS. 5a–c). This choice is motivated by the results from the principal component analysis of all power spectra. In this case, all of the control subjects are directly compared with one another, creating an unbiased grouping of the population Examining FIGS. 5a–c, note that the patients 82 tend to be located over a wide area in low-frequency space with increased global power, whereas normal control subjects 80 are clustered in the higher-frequency space with less global power.

To determine if the increased power in the theta band comes with an increased coherence inside low frequencies, as well as between low and high frequencies, correlation plots are computed for individual patients and control subjects. In FIGS. 6–13, the correlation for a control subject and patients are illustrated with the correlation for the specific control subjects and patients. As is shown in FIGS. 7–13, the increase in theta power in patients is in complete accord with low threshold spiking bursting activity (neuronal bursting activity triggered by changing the neuron trigger threshold), with theta rhythmicity in the medial thalamus of patients with the same diseases, as demonstrated by single-unit recordings during stereotactic surgery.

Moreover, the correlation shown for patients in FIGS. 7–13 shows the harmonics at gamma frequencies, indicating an edge effect. If certain cortical structures in the brain are forced to generate gamma frequencies in a continuous and stereotyped manner, the brain generates cognitive experiences and motor behavior, in the absence of context with the external world and without the intentionality that normally characterizes human function. This edge effect, gamma-band activity is responsible for the positive symptoms reported by the patients whose correlation is shown in FIGS. 7–13.

For the cross-correlation of different frequency spectrums, smaller time periods are used to create a plurality of frequency spectra, which are then cross-correlated to compute the spectral correlation of different frequency spectra. For instance, in an embodiment wherein the total measurement time is 10 minutes, a data window of 5 seconds is used to create 120 frequency spectra ([10 min×60 s/5 s]=120 spectra) that are then cross-correlated to determine the temporal frequency correlation of the neuronal oscillations over time.

Figure 6:
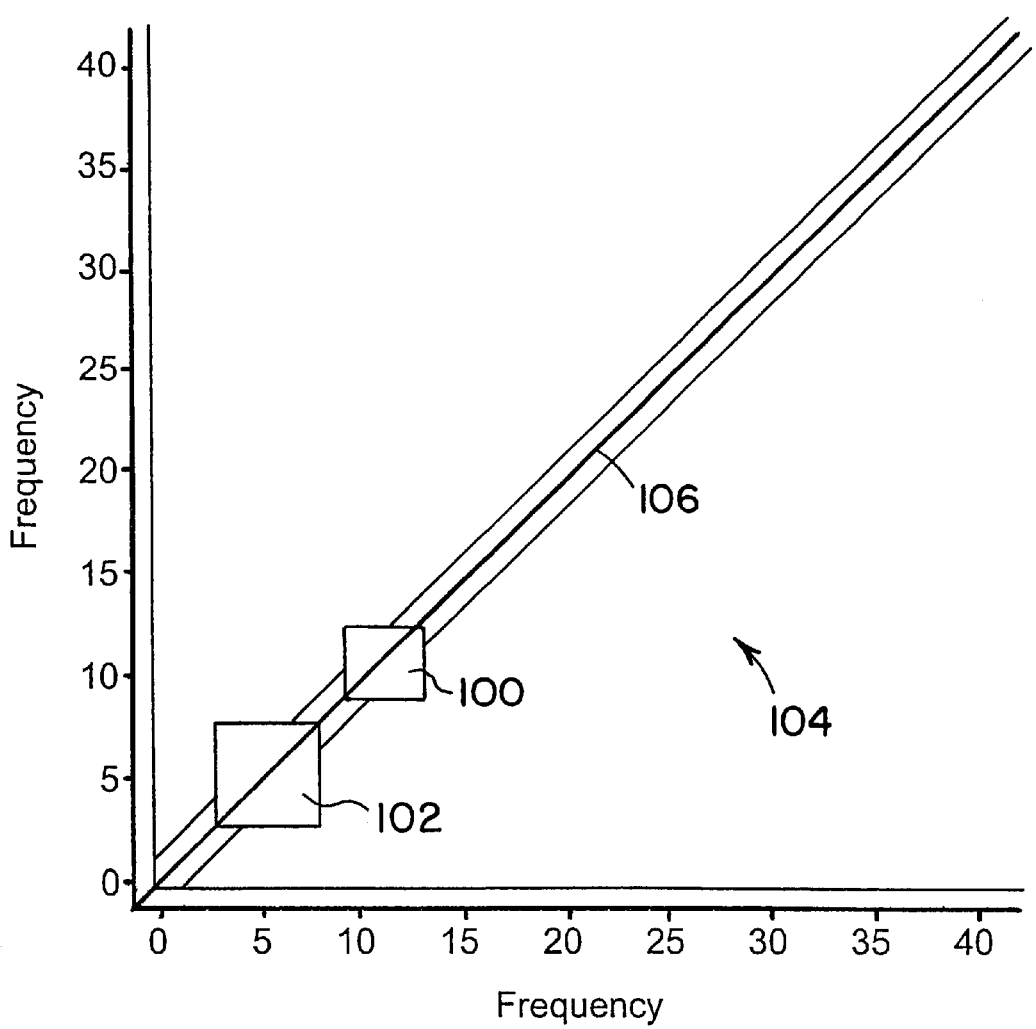
FIG. 6 is a graph illustrative of the Power Spectrum Correlation Regions.

FIG. 6 is a graph of that illustrates the Power Spectrum Correlation Regions. In general, frequency cross-correlation on a frequency—frequency graph relates the correlation of one frequency to that of another. Thus, the unit of measurement for both the horizontal and vertical axes is frequency (Hz), and a cross-correlation plot shows areas of high correlation with light colors and areas of low correlation with dark colors. In addition, a cross-correlation plot forms a mirror image along the diagonal axis that bisects the horizontal and vertical axes, because the correlation a first frequency to a second is identical when the first frequency is plotted on the horizontal and the second frequency is plotted on the vertical, and vice versa.

Turning to FIG. 6, therein is shown an unplotted cross-correlation graph that illustrates particular regions of interest when examining actual cross-correlation plots. The diagonal axis 106 that forms the axis of the mirror image is shown. The first region is the nominal correlation region 100 that includes 10–15 Hz frequency correlations with other 10–15 Hz frequencies. The 10–15 Hz frequencies are where normal correlation peaks occur for individuals that do not have thalamocortical dysrhythmia, and thus a high correlation would be expected in the nominal correlation region 100 for normal individuals. The second region is the theta correlation region 102 that includes 4–8 Hz frequency correlations with other 4–8 Hz frequencies. The 4–8 Hz frequencies are where abnormal correlation peaks occur for patients that have thalamocortical dysrhythmia, and thus a high correlation would be expected in the theta correlation region 102 individuals that have thalamocortical dysrhythmia. The third region is the off-axis correlation region 104 that includes the off-axis (relative to the diagonal axis 106) correlations of frequencies in the theta and gamma bands. The frequency correlation in the off-axis region 104 should be low for normal individuals that do not suffer from thalamocortical dysrhythmia, but will be higher for patients with thalamocortical dysrhythmia because of the abnormal correlation between theta- and gamma-band frequencies caused by thalamocortical dysrhythmia.

The results of the cross correlation of power spectra are shown in FIGS. 7–13. Each of these figures plots the frequency-to-frequency correlation of neuronal oscillation by depicting areas of high correlation as light and areas of low correlation as dark. As mentioned above, the graph forms a mirror image along the diagonal axis that bisects the horizontal and vertical axis. The regions of interest as described in FIG. 6 correspond to the same regions in FIGS. 7–13; thus the degree of correlation within the nominal correlation, theta correlation and off-axis correlation regions may be used to determine if an individual has thalamocortical dysrhythmia.

Figure 7:
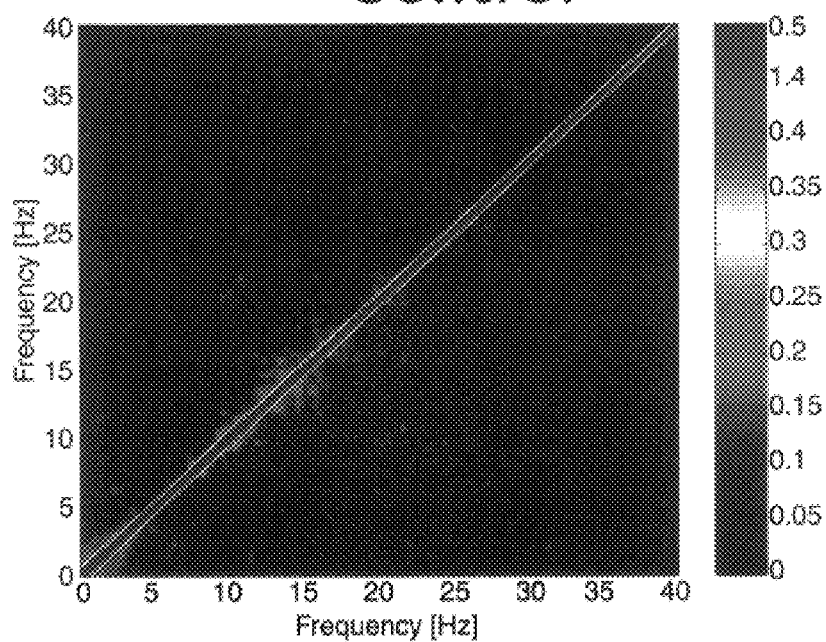
FIG. 7 is a graph of the Power Spectrum Correlation for a Control Subject.

Referring now to FIG. 7, therein is shown the frequency—frequency plot for a control patient that does not suffer from thalamocortical dysrhythmia. The high degree of correlation in the nominal correlation region is notable, as the high correlation corresponds to the single peak at approximately 10–12 Hz depicted in the control subject graphs of FIG. 4. In addition, the low degree of correlation in the theta-correlation region is also notable, as the low correlation indicates the absence of a theta-band peak that would be expected if a low frequency shift to the theta-range had occurred because of thalamocortical dysrhythmia.

Finally, and most significantly, there is no evidence of significant cross-correlation between frequencies in the off-axis correlation region; if thalamocortical dysrhythmia was present, then increased levels of cross-correlation would be present in the cross correlation region because of the temporal coherence between "edge effect" gamma-band oscillations and theta-band oscillations.

Figure 8:
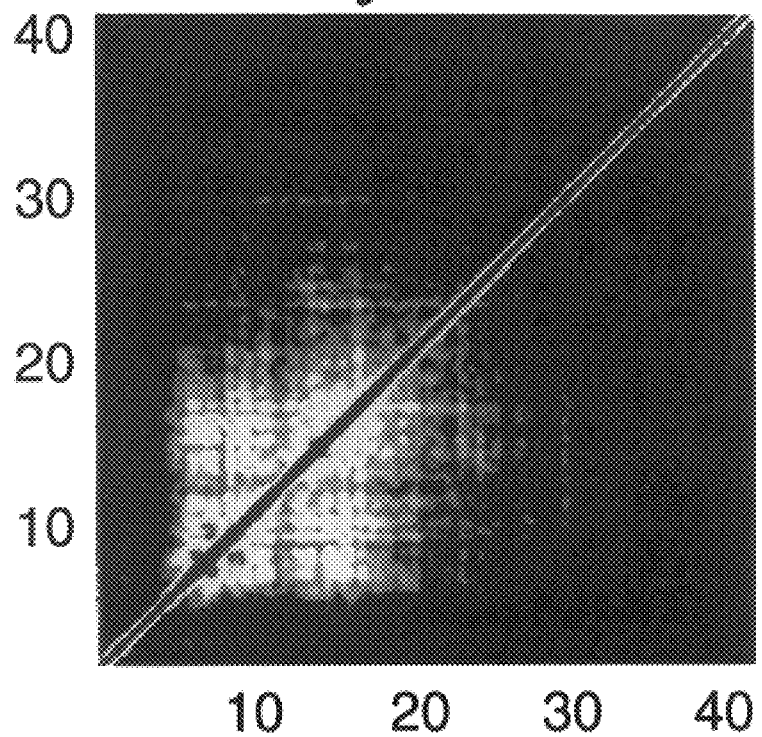
FIG. 8 is a graph of the Power Spectrum Correlation for a Patient with Psychosis.
Figure 11:
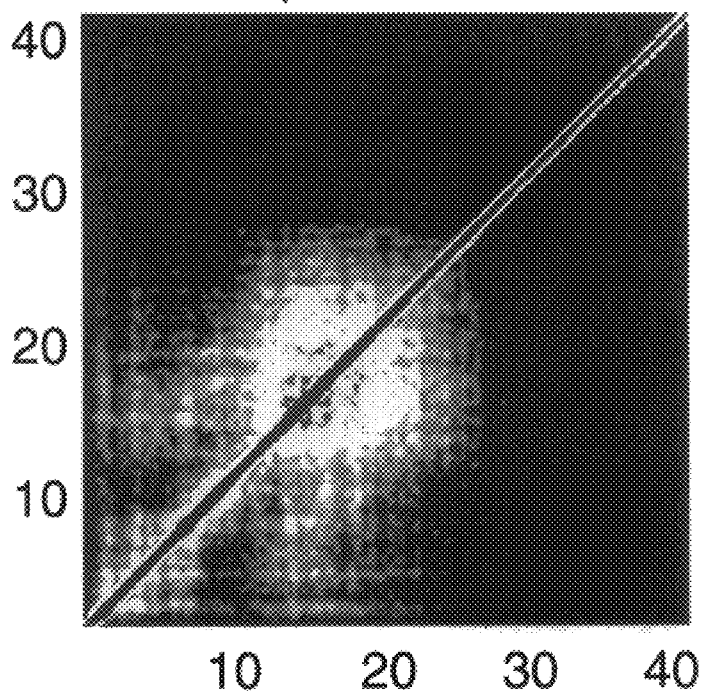
FIG. 11 is a graph of the Power Spectrum Correlation for a Patient with Neuropathic Pain.
Figure 12:
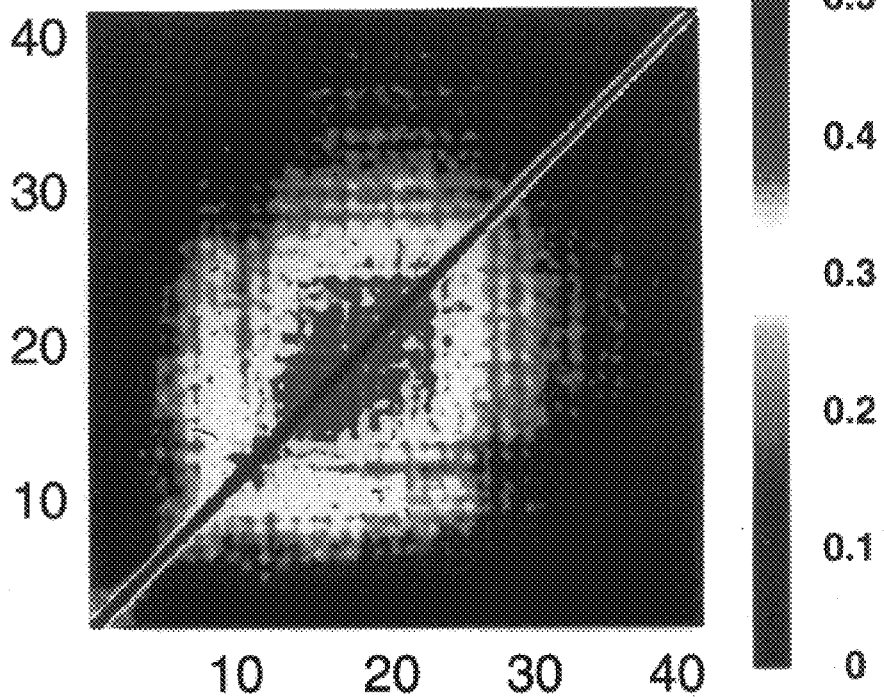
FIG. 12 is a graph of the Power Spectrum Correlation for a Patient with Parkinson's.
Figure 13:
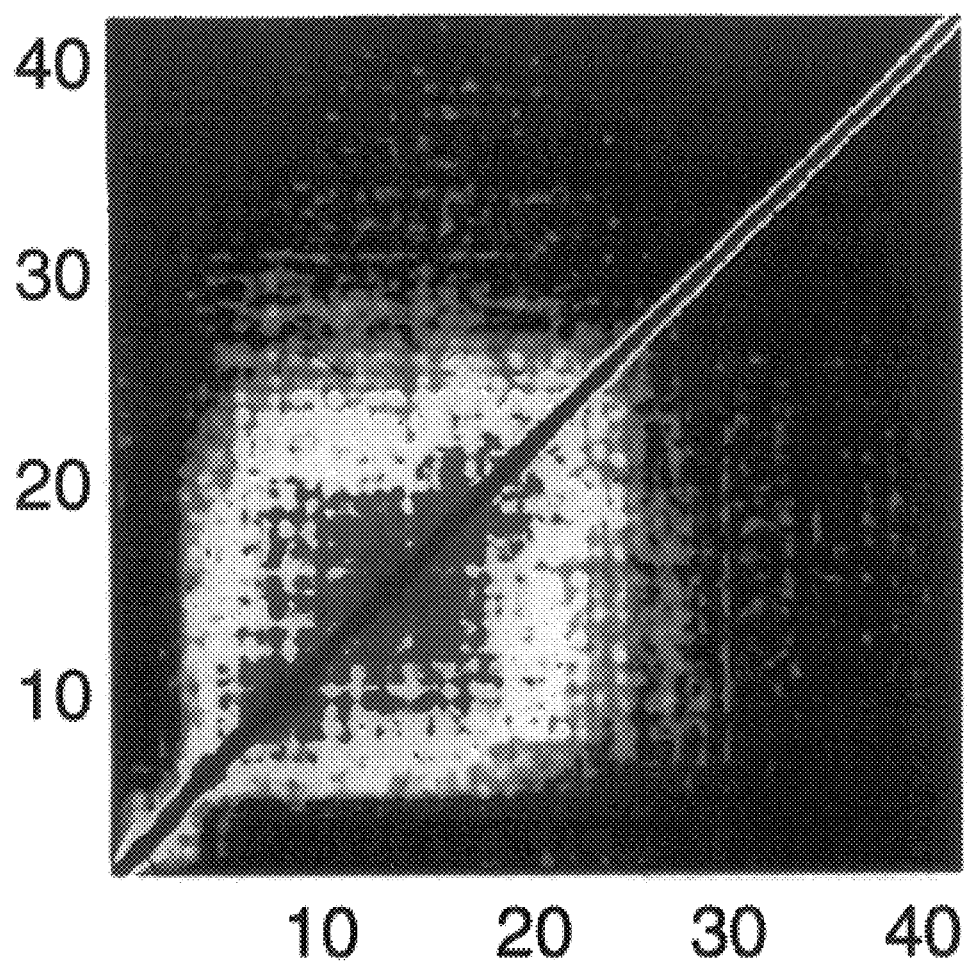
FIG. 13 is a graph of the Power Spectrum Correlation for a Patient with Tinnitus.

In comparison to FIG. 7, FIGS. 8–13 show the cross-correlation of patients that suffer from specific neuropsychological diseases that are caused by thalamocortical dysrhythmia. In particular, FIG. 8 shows the disease psychosis, FIG. 9 shows the disease OCD, FIG. 10 shows the disease depression, FIG. 11 shows the disease neuropathic pain, FIG. 12 shows the disease Parkinson's, and FIG. 13 shows the disease tinnitus. These figures and diseases are not conclusive, but rather illustrative of the general features and properties of neuropsychological diseases caused by thalamocortical dysrhythmia. The neuronal oscillatory characteristics of psychosis, OCD, depression, neuropathic pain and Parkinson's are identical with the exception of the region of the brain wherein characteristics manifest themselves. Thus, the cross-correlation characteristics and features of patients with these and other neuropsychological diseases are similar, and the discussion of FIGS. 8–13 below apply equally to all other neuropsychological diseases caused by thalamocortical dysrhythmia.

Turning to FIGS. 8–13, the cross-correlation of neuropsychological diseases caused by thalamocortical dysrhythmia exhibit common characteristics that contrast with those of the control patient in FIG. 7. First, in the nominal correlation region, there is no significant correlation peak that marks the presence of a frequency peak in this region as is present in a control subject. Second, in there is a noticeable correlation peak in the theta correlation region that is not present in the control subject, and that indicates an amplitude peak in the theta-band. This correlation peak in the theta correlation region depicts the frequency shift to the low-theta band caused by the hyperpolarization of thalamic neurons as manifested at the cortical level. Third, and most notable, there is a dramatic increase in correlation within the off-axis correlation region between widely separated frequencies, including correlation between theta- and gamma-band frequencies. The smallest cross-correlation in the off-axis correlation region is shown for the OCD disease in FIG. 9, wherein the cross-correlation still extends at least 10 Hz off-axis (10–20 Hz continuous cross-correlation). Thus, there are significant increases and decreases of cross-correlation in the regions of interest for patients that suffer from thalamocortical dysrhythmia as compared to control subjects.

In practical terms, the significant increase cross-correlation shown in FIGS. 8–13, particularly within the off-axis correlation region, simply represents the abnormal but simultaneous presence of theta- and gamma-band oscillations in patients that have thalamocortical dysrhythmia. In contrast, the lack of cross-correlation shown in FIG. 7 represents the nominal absence of theta-band oscillation for control subjects that do not have thalamocortical dysrhythmia. The presence or absence of this cross-correlation is one baseline that may be used to determine the presence or absence of thalamocortical dysrhythmia.

Turning again to FIG. 3, a qualitative or quantitative correlation map can be selected as a baseline for the correlation results. The correlation baseline sources selected at step 58 may include the correlation measurements from a control subject or patient; average from a group of subjects or patients, or even a comparison with a patient's prior measurements when the patient was symptomatic or asymptomatic (e.g., a patient who went into treatment but then went into remission). Correlation baselines may also include any other real or artificial baseline derived from a theoretical or actual basis for determining the correlation characteristics of thalamocortical dysrhythmia (e.g., direct modeling of the thalamocortical system itself to derive its characteristics). Once one or more correlation baselines have been selected, then the correlation deviation calculations and analysis can be performed in steps 64 and 66, respectively, to determine qualitatively or quantitatively whether the patient suffers from thalamocortical dysrhythmia.

Figure 14:
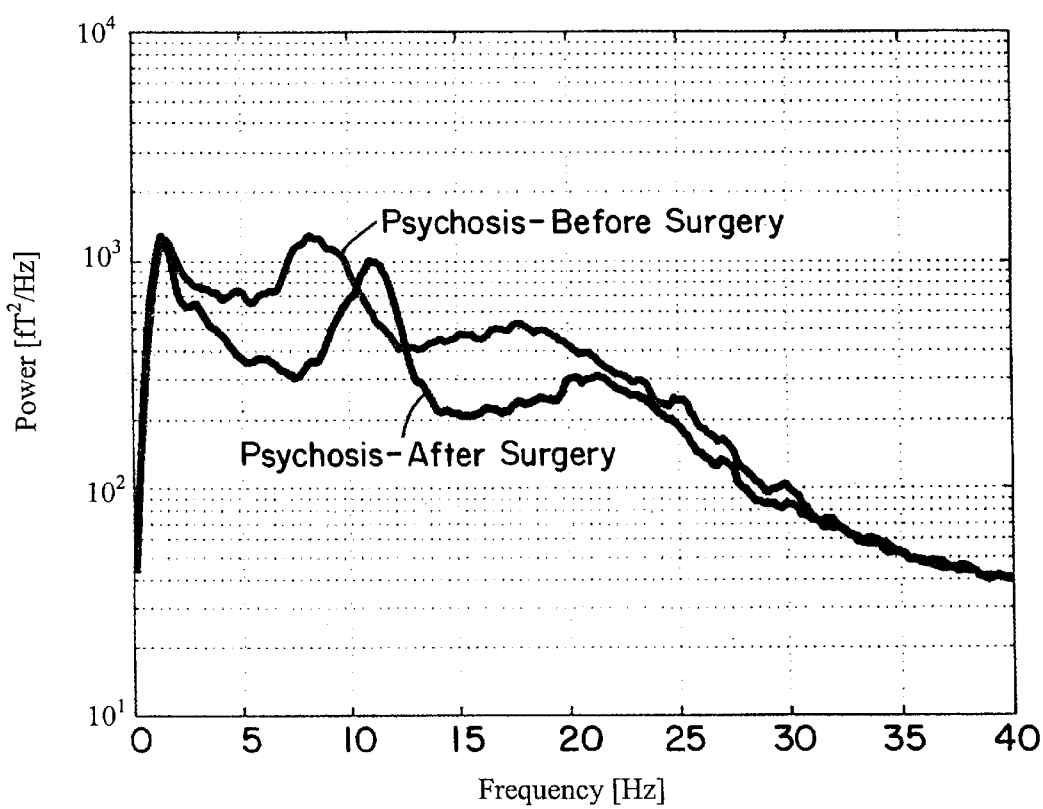
FIG. 14 is a graph of the Power Spectrum of a Patient Pre and Post Treatment.

Upon diagnosis of thalamocortical dysrhythmia at step 70, a patient can be treated by methods including surgery, electrostimulus and/or pharmacological treatment in step 72. The before and after frequency and correlation plots of FIGS. 14 and 15a–d demonstrate the use of the present invention to monitor the effectiveness of the treatment in a fashion similar to the original diagnosis. FIG. 14 shows the frequency spectrum of a patient before and after treatment, whereas FIGS. 15a–d shows the frequency correlation plots of a patient before and after treatment as compared to a control subject.

Examining FIG. 14, the before plot 110 of the patient shows a pre-treatment frequency peak 114 in the 8 Hz range, which is the high-theta band. In contrast, the after plot 112 of the psychosis patient shows a post-treatment frequency peak 116 in the 10 Hz range, which is outside the theta-band. In addition, the overall amplitude of the frequency response has significantly decreased from the before plot 110 to the after plot 112. Thus, it is clear that the treatment has both reduced the hyperpolarization, caused a frequency shift upwards from the theta band, and decreased the overall amplitude of neuronal activity.

Turning to FIGS. 15a–d, the cross-correlation graphs for the pre and post treatment of a patient are shown along with that of a control subject for reference. In the pre-treatment eyes open graph shown in FIG. 15b, the pre-treatment correlation peak resides at approximately 7–8 Hz within the theta correlation region. The pre-treatment eyes closed graph shown in FIG. 15c also shows the correlation in the theta correlation region, as well as significant cross-correlation in the off-axis correlation region. These observations are in contrast with those of the control subject shown in FIG. 15a, which include a correlation peak at the 10 Hz frequency within the nominal correlation region and no significant cross-correlation in the off-axis correlation region.

Figure 15A:
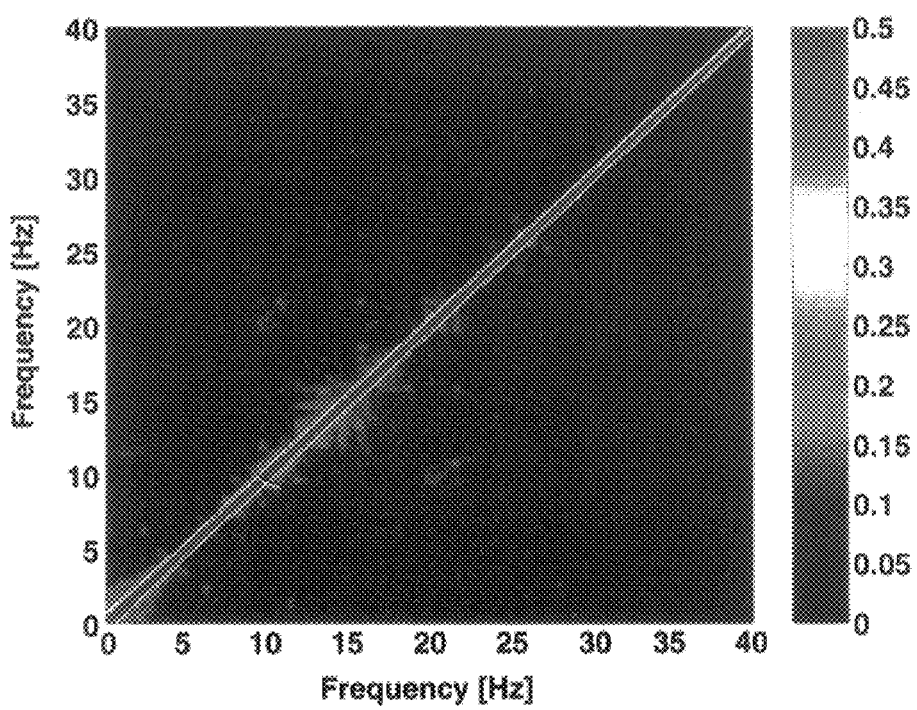
FIGS. 15a–d are graphs of the Power Spectrum Correlation of a Patient Pre- and Post-Treatment.
Figure 15B:
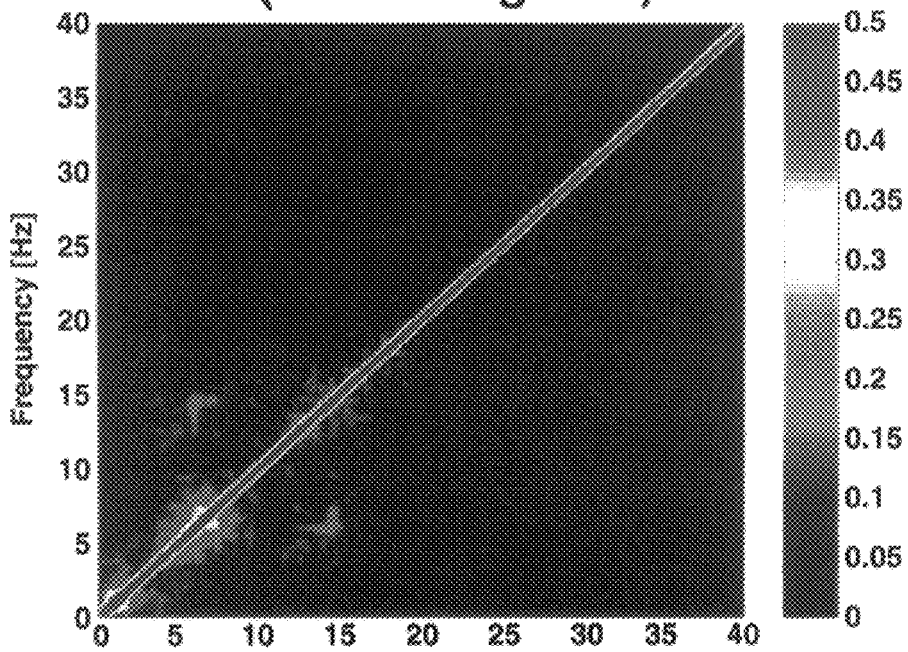
Figure 15C:
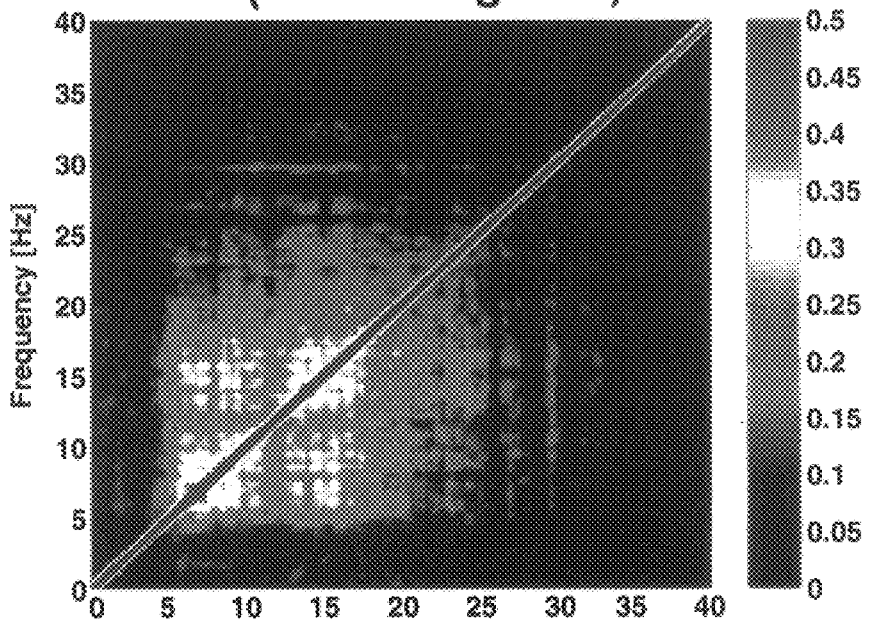
Figure 15D:
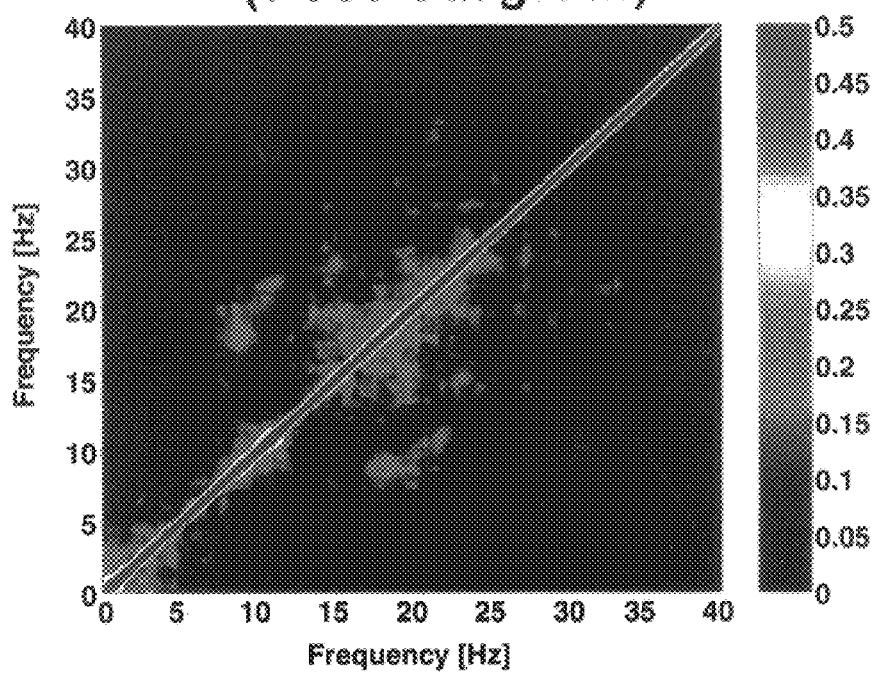

After treatment, the correlation characteristics of the patient have significantly changed both relative to the control subject as shown in FIG. 15a and to the pre-treatment correlations shown in FIGS. 15b–c. The post-treatment eyes closed graph of FIG. 15d now shows a correlation frequency peak around 10 Hz in the nominal correlation region, which represents a positive frequency shift from the theta frequency region shown in FIG. 15b. In addition, the cross-correlation in the off-axis correlation region has significantly decreased after treatment according to FIG. 15d. As compared to the pre-treatment off-axis correlation region shown in FIG. 15c, the post treatment off-axis correlation region in FIG. 15d has significantly decreased and is very similar to the off-axis correlation region 15a of the control subject. Thus, the pre- and post-treatment correlation plots of FIGS. 15a–d demonstrate a post-treatment frequency shift out of the theta-band, as well as a significant decrease in frequency cross-correlation, both of which are associated with thalamocortical dysrhythmia.

It has thus been determined that a common mechanism is operant for the different medical conditions caused by thalamocortical dysrhythmia and that, depending on its localization in the thalamocortical network, it may produce dysfunctions and symptoms ascribed to various common neurological or psychiatric conditions.

From a functional point of view, the common link among these different medical conditions relates to electrophysiological properties of the thalamocortical loops involved. Thus, low-frequency, coherent electrical activity with wide hemispheric representation is common in all patients studied. This low-frequency, thalamocortical activity has a plurality of characteristics that distinguish it from the theta rhythmicity present under normal waking conditions. The first characteristic is the presence of a persistent low-frequency, thalamocortical resonance during the awake state. The second characteristic is the wide coherence of the low-frequency thalamocortical resonance over the recorded channels. The low frequencies themselves are not pathological; they occur as thalamocortical synchronization continuously during delta sleep, and transiently during wakefulness, under specific conditions of mental and emotional activity. Rather, there is an ongoing, low-frequency activity that is present during the entire day and that continuously modifies and limits the dynamic organization of the brain; it does so all the more efficiently because it produces large-scale coherence.

An edge effect generates the high-frequency, gamma band activity that is the origin of the appearance of clinical symptoms and signs (FIG. 2). The basic hypothesis, as illustrated in FIG. 2, proposes that protracted hyperpolarization of a specific nucleus will result in low-frequency oscillation at the theta frequency band. Such oscillation, by activating the return corticothalamic pathways, will entrain, through the reticular nucleus and through direct thalamic activation, the non-specific system. The result is the promotion of large-scale, low-frequency oscillatory coherence. At the cortical level, the reduction of lateral inhibition promotes coherent gamma-band oscillation and thus positive symptoms. Note that both deep brain stimulation and thalamic lesions aim at reducing the nonspecific component of this pathway. The present discussion regarding the gamma-band oscillation is based on the many studies indicating that perceptual, cognitive, and motor experiences are associated with such activity. The term "edge effect" was coined in the consideration of the aura that accompanies migraine attacks and is seen most notably in the visual cortex. During this condition, a wave of depolarization generating the scotoma is surrounded by an edge of excitation that produces the bright visual illumination known as a "halo." This halo is the manifestation of the interface between the area of depolarization and the unaffected area that surrounds the malfunction site.

The neurological or psychiatric manifestations of patients are conditioned by the localization of the primary lesion. Thus, in the case of Parkinsonism, in which low-frequency activity is present, excess inhibition, produced by hyperactive palladial input onto the motor thalamus, produces hyperpolarization of thalamic relay cells, with the consecutive de-inactivation of T-channels and the appearance of low-threshold calcium spiking and low-frequency oscillation. This oscillation produces then the edge effect, which generates the clinical Parkinsonian manifestations. This is the case, because the reduction of thalamic overinhibition, by surgical decrease of the pallidal output to thee thalamus, diminishes or suppresses Parkinsonian manifestations. This therapeutic goal can be reached by a radio-frequency lesion and a chronic stimulation device that causes a continuous depolarization block, or by pharmacological treatment to reduce excess inhibition. In other words, reduction of the thalamic overinhibition suppresses the thalamocortical dysrhythmia that is responsible for clinical symptomatology. This is directly supported by the single-unit recordings taken during stereotactic operations that show the present of low threshold spike bursting activity in the pallidal-recipient, motor-thalamic nuclei of Parkinsonian patients.

A similar case may be made for other conditions. Indeed, in the cases of neurogenic pain, depression, and tinnitus, a persistent and coherent theta-band thalamocortical oscillatory activity is also observed. In these three clinical situations, but also in epilepsy, obsessive-compulsive disease, dystonia, and spasticity, medial thalamic low threshold spike theta-band rhythmic activity is shown, as well as the possibility of reducing the symptoms by a stereotactic intervention at the medial thalamic level. In the field of psychiatry, in addition to obsessive-compulsive disease and depression, low-frequency activity has also been known to ve recorded in schizophrenic patients, although a thalamocortical dysrhythmia was never considered as a mechanism.

As is described above, the basic idea infers that the symptomatology presented by the patients ultimately relates to the overall localization of the low-frequency activity. What is observed is an abnormal distribution and coherence of low-frequency activity over wide areas of the brain, anterior as well as posterior, and the persistence of this phenomenon throughout the recording session. Thus, in the case of a depressed patient, stimuli that may produce short-lived sadness in normal individuals may have a dynamic time course that prolongs the normal emotional experience into long-lasting depressive periods. Such experience may occur even after exposure to stimuli that are not normally depressant. Similar conclusions may be reached concerning all of the other thalamocortical dysrhythmias described here, such as the exacerbation of neurogenic pain by nonpainful, tactile, or proprioceptive stimuli.

An amplification of the symptomatology caused by fear and stress is also recognized by patients suffering from the various positive symptoms described herein. In view of the widespread distribution of the coherent thalamocortical theta-band activity described here, the large assocational-mesocortical system is more relevant than lateral unimodal cortical areas. The areas where maximal low-frequency activity is expected are the cingulate, medial prefrontal, and orbitofrontal cortices for neuropsychiatric symptoms; the supplementary motor and cingulate areas for Parkinson's disease; the insular, parietal opercular, and cingular cortices for neurogenic pain; and the medial temporal areas for tinnitus.

In terms of thalamocortical dynamics, the medial thalamic nuclei might be seen as the best candidates in view of their better coherence abilities. However, thalamic dynamics relates essentially to the temporal interactions between the "content, specific or lateral" and the "context, nonspecific or medial" thalamocortical systems. In this sense the relevance of the generation of thalamocortical dysrhythmia must be ascribed to both systems.

Thalamocortical dysrhythmia is characterized as central and the abnormal condition is brought about by changes in intrinsic, voltage-gated ionic conductances at the level of thalamic relay cells, namely, the deinactivation of T channels by cell membrane hyperpolarization. Low threshold spike bursts are produced and lock the related thalamocortical circuits in low-frequency resonance. Low-frequency loops interact at the cortical level with high-frequency ones, giving rise to the edge effect and the generation of positive symptoms. In tinnitus peripheral neurogenic pain, Parkinson's disease, and some neuropsychiatric disorders with striatal origin, the dysrhythmic mechanism is triggered bottom up, i.e., from the thalamus toward the cortex. In other situations, such as epilepsy, neuropsychiatric conditions of cortical origin, and central cortical neurogenic pain, the mechanism may be top-down, triggered by a reduction of the corticothalamic input. Both bottom-up and top-down situations should result in excess inhibition or disfacilitation, generating thalamic cell membrane hyperpolarization and low-frequency oscillation.

A proper analysis of the thalamocortical dysrhythmia should be implemented with a technique that is fast enough to distinguish among the different thalamocortical frequencies (4–50 Hz, and it must have sufficient spatial resolution to localize accurately all sites involved. These criteria seem to be ideally fulfilled by MEG. However, considering the enormous diagnostic relevance of both PET and functional MRI, another approach may be to combine these three noninvasive tools, such that their relative advantages may coordinate to optimize understanding and diagnosis of these abnormal conditions. When comparing MEG results with those obtained by PET recordings, it is evident that low-frequency activity in MEG correlates with hypometabolism in PET, which is expected in view of the decreased electrical activity accompanying calcium-dependant potassium conductances. PET may demonstrate high-frequency edge-effect activation areas as hypermetabolic, and low-frequency areas as hypometabolic. This proposition is already supported by reports of both hyper- and hypometabolic areas in the thalamus and cortex of patients suffering from neurogenic pain. On the other hand, functional MRI may prove to be a powerful tool for localizing areas that harbor elevated gamma-band activity, if such elevation leads to elevated metabolic activity.

While the invention has been particularly shown and described with reference to preferred embodiments thereof, it will be understood by those skilled in the art that various changes in form and details may be made therein without departing from the spirit and scope of the invention.

We claim:

1. A method for diagnosing thalamacortical dysrhythmia, comprising the following steps:
   measuring electromagnetic activity of a cortical brain region;
   determining the spectral content of the electromagnetic activity of the cortical brain region;
   determining whether the spectral content includes an increase in either signal level of the electromagnetic activity or a ratio of theta-band to gamma-band oscillations, relative to a reference level; and
   diagnosing thalamacortical dysrhythmia if it is determined that the spectral content includes an increase in either signal level of the electromagnetic activity or a ratio of theta-band to gamma-band oscillations, relative to the reference level;
   wherein the step of determining the spectral content includes a determination of a spectral content of at least the gamma band.

2. The method of claim 1, further comprising the steps of removing cardiac artifacts and external noise.

3. The method of claim 1, further comprising the step of utilizing a magnetoencepholograph to perform the measuring step.

4. The method of claim 1, further comprising the step of utilizing a PET device to perform the measuring step.

5. The method of claim 1, wherein the reference level corresponds to a subject's own level without the presence of the dysrhythmia.

6. The method of claim 1, wherein the reference level corresponds to a level without the presence of the dysrhythmia as obtained from one or more different individuals.

7. The method of claim 1, wherein the step of determining whether the spectral content includes an increase in either signal level of the electromagnetic activity or a ratio of theta-band to gamma-band oscillations, is indicative of an abnormal input to a thalamic brain portion, which in turn causes neuronal hyperpolarization, which results in thalamic oscillations at a theta-band frequency range, the thalamic oscillations in turn causing theta-band frequency range oscillations in the cortical brain region via corticothalamic pathways.

8. The method of claim 1, further comprising the step of determining whether an abnormal input is provided to a thalamic brain portion.

9. The method of claim 1, further comprising the step of determining whether thalamic oscillations occur at a theta-band frequency.

10. The method of claim 1, further comprising the step of determining whether theta-band frequency oscillations occur in the cortical brain region.

11. The method of claim 1, further comprising the step of determining whether a reduction of lateral inhibition in a first portion of the brain promotes coherent gamma-band oscillations in a different portion of the brain.

12. A method for diagnosing thalamacortical dysrhythmia, comprising the following steps:
    measuring electromagnetic activity of a cortical brain region;
    determining the spectral content of the electromagnetic activity of the cortical brain region;
    determining whether the spectral content includes a shift in neuronal oscillation to a lower frequency range relative to a reference level; and
    diagnosing thalamacortical dysrhythmia if it is determined that the spectral content includes a shift in neuronal oscillation to a lower frequency range relative to the reference level;
    wherein the step of determining the spectral content includes a determination of a spectral content of at least the gamma band.

13. The method of claim 12, further comprising the additional step of providing treatment for the dysrhythmia in the form of at least one of: surgical treatment, electrical treatment, and pharmacological treatment.

14. The method of claim 12, comprising the additional step of determining the dysrhythmia to be at least one of: neurogenic pain, obsessive compulsive disorder, depression, panic disorder, Parkinson's disease, schizophrenia, rigidity, dystonia, tinnitus, and epilepsy.

15. The method of claim 12, wherein the step of determining whether the spectral content includes a shift in neuronal oscillation to a lower frequency range relative to a reference level is indicative of an abnormal input to a thalamic brain portion, which in turn causes neuronal hyperpolarization, which results in thalamic oscillations at a theta-band frequency range, the thalamic oscillations in turn causing theta-band frequency range oscillations in the cortical brain region via corticothalamic pathways.

16. The method of claim 12, further comprising the step of determining whether an abnormal input is provided to a thalamic brain portion.

17. The method of claim 12, further comprising the step of determining whether thalamic oscillations occur at a theta-band frequency.

18. The method of claim 12, further comprising the step of determining whether theta-band frequency oscillations occur in the cortical brain region.

19. The method of claim 12, wherein a reduction of lateral inhibition in a first portion of the brain promotes coherent gamma-band oscillations in a different portion of the brain.

20. A method for diagnosing thalamacortical dysrhythmia, comprising the following steps:

measuring electromagnetic activity of a cortical brain region at a plurality of different points in time;

determining the spectral content of the electromagnetic activity of the cortical brain region at each point in time;

determining whether the spectral content includes a coherence between low frequency range oscillations and high frequency range oscillations; and diagnosing thalamacortical dysrhythmia if it is determined that the spectral content includes a coherence between low frequency range oscillations and high frequency range oscillations;

wherein the step of determining the spectral content includes a determination of a spectral content of at least the gamma band.

21. The method of claim 20 wherein the low frequency range includes the theta-band and the high frequency range includes the gamma-band.

22. The method of claim 21, wherein the step of determining whether the spectral content includes a coherence between low frequency range oscillations and high frequency range oscillations includes the step of generating a frequency—frequency plot.

23. The method of claim 20, wherein the measuring step is carried out at a plurality of different cortical regions, further comprising the additional step of identifying at least one specific cortical region where a dysrhythmia is present.

24. The method of claim 20, comprising the additional step of determining the dysrhythmia to be at least one of: neurogenic pain, obsessive compulsive disorder, depression, panic disorder, Parkinson's disease, schizophrenia, rigidity, dystonia, tinnitus, and epilepsy.

25. The method of claim 20, wherein the step of determining whether the spectral content includes a coherence between low frequency range oscillations and high frequency range oscillations is indicative of an abnormal input to a thalamic brain portion, which in turn causes neuronal hyperpolarization, which results in thalamic oscillations at a theta-band frequency range, the thalamic oscillations in turn causing theta-band frequency range oscillations in the cortical brain region via corticothalamic pathways.

26. The method of claim 20, further comprising the step of determining whether an abnormal input is provided to a thalamic brain portion.

27. The method of claim 20, further comprising the step of determining whether thalamic oscillations occur at a theta-band frequency.

28. The method of claim 20, further comprising the step of determining whether theta-band frequency oscillations occur in the cortical brain region.

29. The method of claim 20, wherein a reduction of lateral inhibition in a first portion of the brain promotes coherent gamma-band oscillations in a different portion of the brain.

30. A method for diagnosing thalamocortical dysrhythmia, said method comprising the steps of:

measuring neuronal oscillations, filtering said neuronal oscillations, transforming said filtered neuronal oscillations into the frequency domain, cross-correlating said frequency domain neuronal oscillation measurements, selecting at least one baseline as a reference with which to compare at least one of said frequency domain neuronal oscillation measurements and said cross-correlated neuronal oscillation measurements, determining the deviation of at least one of said frequency domain neuronal oscillation measurements and said cross-correlated neuronal oscillation measurements from at least one of said baselines; and determining if thalamocortical dysrhythmia is present based on at least one of said deviation determinations.

31. The method of claim 30, wherein said neuronal oscillations are measured at the cortical level.

32. The method of claim 30, wherein said neuronal oscillation measurements are filtered to remove cardiac artifacts and external noise artifacts.

33. The method of claim 30, wherein said baseline references include the neuronal oscillation characteristics of at least one individual without thalamocortical dysrhythmia.

34. The method of claim 30, wherein said baseline references include the neuronal oscillation characteristics of at least one individual with thalamocortical dysrhythmia.

35. The method of claim 30, wherein at least one baseline reference is a threshold that acts as a threshold value relative to said neuronal oscillation measurements.

36. The method of claim 30, wherein at least two of said deviations from said baselines are determined, and wherein said deviations from said baselines are then weighted and summed to determine if thalamocortical dysrhythmia is present.

37. The method of claim 30, including the step of treating individuals determined to have thalamocortical dysrhythmia, and wherein said treatment may include at least one of the treatment methods including surgery, electrostimulation, and pharmacological treatment.

* * * * *